(12) United States Patent
Grubac et al.

(10) Patent No.: US 11,684,776 B2
(45) Date of Patent: Jun. 27, 2023

(54) FIXATION COMPONENT FOR MULTI-ELECTRODE IMPLANTABLE MEDICAL DEVICE

(71) Applicant: Medtronic, Inc., Minneapolis, MN (US)

(72) Inventors: Vladimir Grubac, Brooklyn Park, MN (US); Jeffrey S. Voss, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 63 days.

(21) Appl. No.: 16/990,239

(22) Filed: Aug. 11, 2020

(65) Prior Publication Data

US 2021/0046306 A1 Feb. 18, 2021

Related U.S. Application Data

(60) Provisional application No. 62/885,843, filed on Aug. 13, 2019.

(51) Int. Cl.
*A61N 1/05* (2006.01)
*A61N 1/362* (2006.01)
(Continued)

(52) U.S. Cl.
CPC ............ *A61N 1/0573* (2013.01); *A61B 5/283* (2021.01); *A61B 5/686* (2013.01); *A61N 1/362* (2013.01); *A61N 2001/058* (2013.01)

(58) Field of Classification Search
CPC .... A61N 1/0573; A61N 1/362; A61N 1/3756; A61N 1/37518; A61N 1/37205;
(Continued)

(56) References Cited

U.S. PATENT DOCUMENTS 3,814,104 A 6/1974 Irnich et al.
3,943,936 A 3/1976 Rasor et al.
(Continued)

FOREIGN PATENT DOCUMENTS

DE 202019105583 U1 11/2019
WO 2002022202 A2 3/2002
(Continued)

OTHER PUBLICATIONS

International Search Report and Written Opinion of International Application No. PCT/US2020/045857, dated Nov. 6, 2020, 8 pp.
(Continued)

*Primary Examiner* — Gary Jackson
*Assistant Examiner* — Alexander M Eisenberg
(74) *Attorney, Agent, or Firm* — Shumaker & Sieffert, P.A.

(57) ABSTRACT

An example fixation component for an implantable medical device (IMD) includes a base and tines extending from the base and being spaced apart from one another. The tines include a penetrator tine and a protector tine. The penetrator tine includes a curved section defining a deformable preset curvature that extends laterally from a proximal section that is fixed to the base, traversing a longitudinal axis of the fixation component, to a distal section that terminates in an incisive distal end that is configured to penetrate a tissue to form a puncture. The protector tine includes a curved section defining a deformable preset curvature that extends from a proximal section that is fixed to the base, outward from the longitudinal axis, to a distal section that terminates in a non-incisive distal end that is configured to pass through the puncture.

33 Claims, 17 Drawing Sheets

(51) Int. Cl.
*A61B 5/00* (2006.01)
*A61B 5/283* (2021.01)
(58) Field of Classification Search
CPC .. A61N 1/375; A61N 2001/058; A61B 5/283; A61B 5/686
See application file for complete search history.

(56) References Cited

U.S. PATENT DOCUMENTS

| | | | |
|---|---|---|---|
| 4,103,690 | A | 8/1978 | Harris |
| 4,142,530 | A | 3/1979 | Wittkampf |
| 4,269,198 | A | 5/1981 | Stokes |
| 4,280,512 | A | 6/1981 | Karr et al. |
| 4,590,949 | A | 5/1986 | Pohndorf |
| 4,858,623 | A | 8/1989 | Bradshaw et al. |
| 4,936,823 | A | 6/1990 | Colvin |
| 5,193,540 | A | 3/1993 | Schulman et al. |
| 5,411,535 | A | 5/1995 | Fujii et al. |
| 5,573,540 | A | 11/1996 | Yoon |
| 5,683,447 | A | 11/1997 | Bush et al. |
| 6,007,558 | A | 12/1999 | Ravenscroft et al. |
| 6,151,525 | A | 11/2000 | Soykan et al. |
| 6,240,322 | B1 | 5/2001 | Peterfeso et al. |
| 6,286,512 | B1 | 9/2001 | Loeb et al. |
| 6,409,674 | B1 | 6/2002 | Brockway et al. |
| 6,575,967 | B1 | 6/2003 | Leveen et al. |
| 6,783,499 | B2 | 8/2004 | Schwartz |
| 6,915,149 | B2 | 7/2005 | Ben-Haim |
| 6,978,178 | B2 | 12/2005 | Sommer et al. |
| 7,290,743 | B2 | 11/2007 | Nowack |
| 7,418,298 | B2 | 8/2008 | Shiroff et al. |
| 8,353,940 | B2 | 1/2013 | Benderev |
| 9,526,522 | B2 | 12/2016 | Wood et al. |
| 10,099,050 | B2 | 10/2018 | Chen et al. |
| 2002/0103424 | A1 | 8/2002 | Swoyer et al. |
| 2002/0165589 | A1 | 11/2002 | Imran et al. |
| 2003/0088301 | A1 | 5/2003 | King |
| 2004/0147973 | A1 | 7/2004 | Hauser |
| 2004/0230281 | A1 | 11/2004 | Heil et al. |
| 2006/0084965 | A1 | 4/2006 | Young |
| 2006/0085039 | A1 | 4/2006 | Hastings et al. |
| 2006/0085041 | A1 | 4/2006 | Hastings et al. |
| 2007/0021813 | A1* | 1/2007 | Sommer ............... A61N 1/0575 607/127 |
| 2007/0135883 | A1* | 6/2007 | Drasler ............... A61B 5/6848 607/126 |
| 2009/0082828 | A1 | 3/2009 | Ostroff |
| 2011/0270340 | A1 | 11/2011 | Pellegrini et al. |
| 2012/0172892 | A1* | 7/2012 | Grubac ............... A61N 1/0573 606/129 |
| 2014/0039591 | A1 | 2/2014 | Drasler et al. |
| 2015/0039070 | A1 | 2/2015 | Kuhn et al. |
| 2015/0039071 | A1* | 2/2015 | Grubac ............... A61N 1/0573 607/128 |
| 2015/0045868 | A1* | 2/2015 | Bonner ............... A61N 1/0573 607/126 |
| 2016/0059003 | A1* | 3/2016 | Eggen ............... A61N 1/3756 606/129 |
| 2017/0106185 | A1* | 4/2017 | Orts ............... A61N 1/3756 |
| 2017/0209688 | A1* | 7/2017 | Drake ............... A61N 1/057 |
| 2017/0209689 | A1* | 7/2017 | Chen ............... A61N 1/3756 |
| 2018/0050208 | A1* | 2/2018 | Shuros ............... A61N 1/37512 |
| 2018/0207434 | A1 | 7/2018 | Webb et al. |
| 2018/0280686 | A1 | 10/2018 | Shuros et al. |
| 2019/0054288 | A1 | 2/2019 | Grubac et al. |
| 2019/0083779 | A1 | 3/2019 | Yang et al. |
| 2019/0083801 | A1* | 3/2019 | Yang ............... A61N 1/0573 |
| 2019/0192863 | A1* | 6/2019 | Koop ............... A61N 1/3756 |
| 2020/0306522 | A1 | 10/2020 | Chen et al. |
| 2020/0306530 | A1 | 10/2020 | Koop et al. |
| 2020/0338356 | A1 | 10/2020 | Anderson et al. |
| 2020/0353242 | A1 | 11/2020 | Drake et al. |
| 2021/0046306 | A1 | 2/2021 | Grubac et al. |
| 2021/0069491 | A1 | 3/2021 | Grubac et al. |
| 2021/0236814 | A1 | 8/2021 | Anderson et al. |
| 2021/0275824 | A1* | 9/2021 | Rock ............... A61N 1/37518 |
| 2022/0062630 | A1 | 3/2022 | Yang et al. |

FOREIGN PATENT DOCUMENTS

| | | |
|---|---|---|
| WO | 2006118865 A2 | 11/2006 |
| WO | 2021030392 A1 | 2/2021 |

OTHER PUBLICATIONS

U.S. Appl. No. 16/825,143, filed Mar. 20, 2020, naming inventors Chen et al.

U.S. Appl. No. 16/847,315, filed Apr. 13, 2020, naming inventors Drake et al.

Haqqani et al., "The Implantable Cardioverter-Defibrillator Lead: Principles, Progress and Promises," PACE, vol. 32, Oct. 2009, pp. 1336-1353.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

* cited by examiner

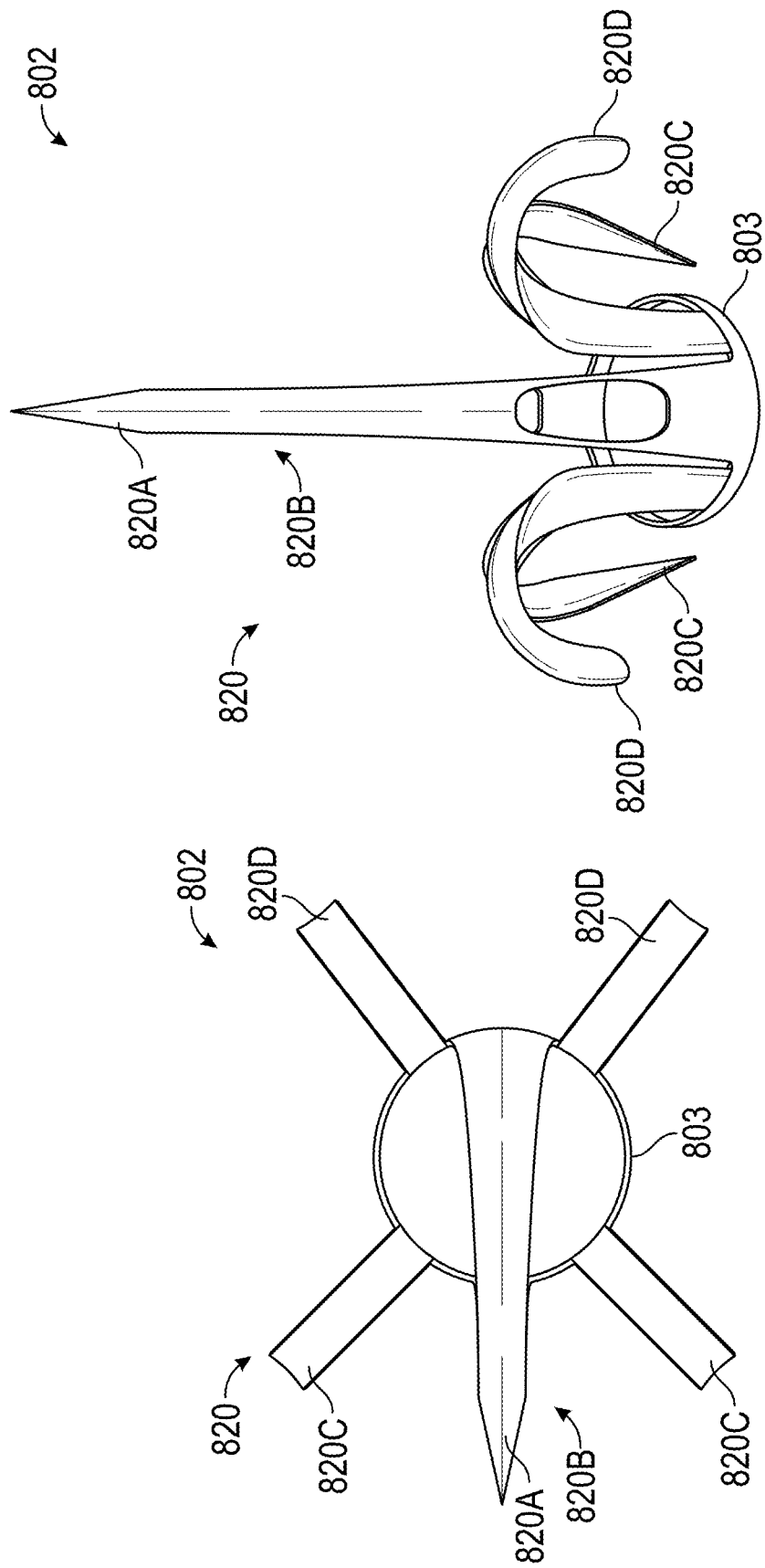

FIXATION COMPONENT FOR MULTI-ELECTRODE IMPLANTABLE MEDICAL DEVICE

This application claims the benefit of U.S. Provisional Application Ser. No. 62/885,843, entitled "FIXATION COMPONENT FOR MULTI-ELECTRODE IMPLANTABLE MEDICAL DEVICE," and filed on Aug. 13, 2019, the entire content of which is incorporated herein by reference.

TECHNICAL FIELD

This disclosure is related to medical device systems, such as relatively compact implantable medical devices and associated fixation components.

BACKGROUND

In some examples, implantable cardiac pacemakers include a pulse generator device to which one or more flexible elongate lead wires are coupled. The pulse generator device may be implanted in a subcutaneous pocket, remote from the heart, and each of the one or more lead wires extends therefrom to a corresponding electrode, coupled thereto and positioned at a pacing site, either endocardial or epicardial. Mechanical and/or MM compatibility issues may be associated with elongate lead wires. Relatively compact implantable medical devices (IMDs) have been developed that are wholly contained within a relatively compact package, the entirety of which is configured for implant in close proximity to the pacing site, e.g., within a chamber of the heart.

SUMMARY

This disclosure describes fixation components, such as fixation components for IMDs, including relatively compact IMDs. An example fixation component has a plurality of tines, including a penetrator tine and a protector tine. The penetrator tine and the protector tine may operate in conjunction with one or more elongate electrodes (e.g., a leadlet) mounted in proximity to a distal end of an 1 MB. For example, the penetrator tine and the protector tine may define an exoskeleton of a cardiac pacing electrode. When deployed, the plurality of tines may provide improved tissue fixation, improved penetration to a selected depth within a tissue, improved electrode contact with selected tissues, and/or improved tissue disengagement compared to fixation components without the described penetrator tine and/or protector tine. In this way, the fixation component may facilitate implanting and/or extracting IMDs.

In some examples, a fixation component for an implantable medical device (IMD) may include a base and a plurality of tines. The base defines a longitudinal axis of the fixation component, and is fixedly attached to the IMD having a proximal end and a distal end aligned along the longitudinal axis. The plurality of tines extend from the base and being spaced apart from one another. The plurality of tines include a penetrator tine and a protector tine. The penetrator tine includes a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to pierce a tissue. The protector tine includes a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end.

In some examples, an implantable medical device (IMD) may include a housing extending along a longitudinal axis from a proximal end to a distal end; an elongate leadlet extending from a proximal end of the leadlet mounted in proximity to the distal end of the housing to a distal end of the leadlet, where the distal end of the leadlet comprises a first electrode; a second electrode mounted in proximity to the distal end of the housing; and a fixation component. The fixation component includes a base and a plurality of tines. The base defines a longitudinal axis of the fixation component, and is fixedly attached to the IMD having a proximal end and a distal end aligned along the longitudinal axis. The plurality of tines extend from the base and being spaced apart from one another. The plurality of tines include a penetrator tine and a protector tine. The penetrator tine includes a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to pierce a tissue. The protector tine includes a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end.

In some examples, a medical device system may include an implantable medical device (IMD) and a delivery tool. The IMD may include a housing extending along a longitudinal axis from a proximal end to a distal end; an elongate leadlet extending from a proximal end of the leadlet mounted in proximity to the distal end of the housing to a distal end of the leadlet, wherein the distal end of the leadlet comprises a first electrode; a second electrode mounted in proximity to the distal end of the housing; and a fixation component including a base in proximity to the distal end of the housing and a plurality of tines fixedly attached spaced from one another around a perimeter of the distal end of the housing. The delivery tool may include a tubular sidewall that defines a lumen into which the IMD may be loaded, where the lumen having a distal opening through which the IMD may be deployed. The plurality of tines of the fixation component include a penetrator tine and a protector tine. The penetrator tine includes a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to pierce a tissue. The protector tine includes a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end.

In some examples, a method of forming a fixation component for an IMD may include forming a base defining a longitudinal axis of the fixation component; and forming a plurality of tines extending from the base and being spaced apart from one another. The plurality of tines include a penetrator tine and a protector tine. The penetrator tine includes a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to pierce a tissue. The protector tine includes a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end.

The details of one or more examples are set forth in the accompanying drawings and the description below. Other features, objects, and advantages will be apparent from the description and drawings, and from the claims.

BRIEF DESCRIPTION OF DRAWINGS

FIGS. 8A and 8B are conceptual diagrams illustrating an example fixation component that includes deployment tines.

DETAILED DESCRIPTION

Figure 1:
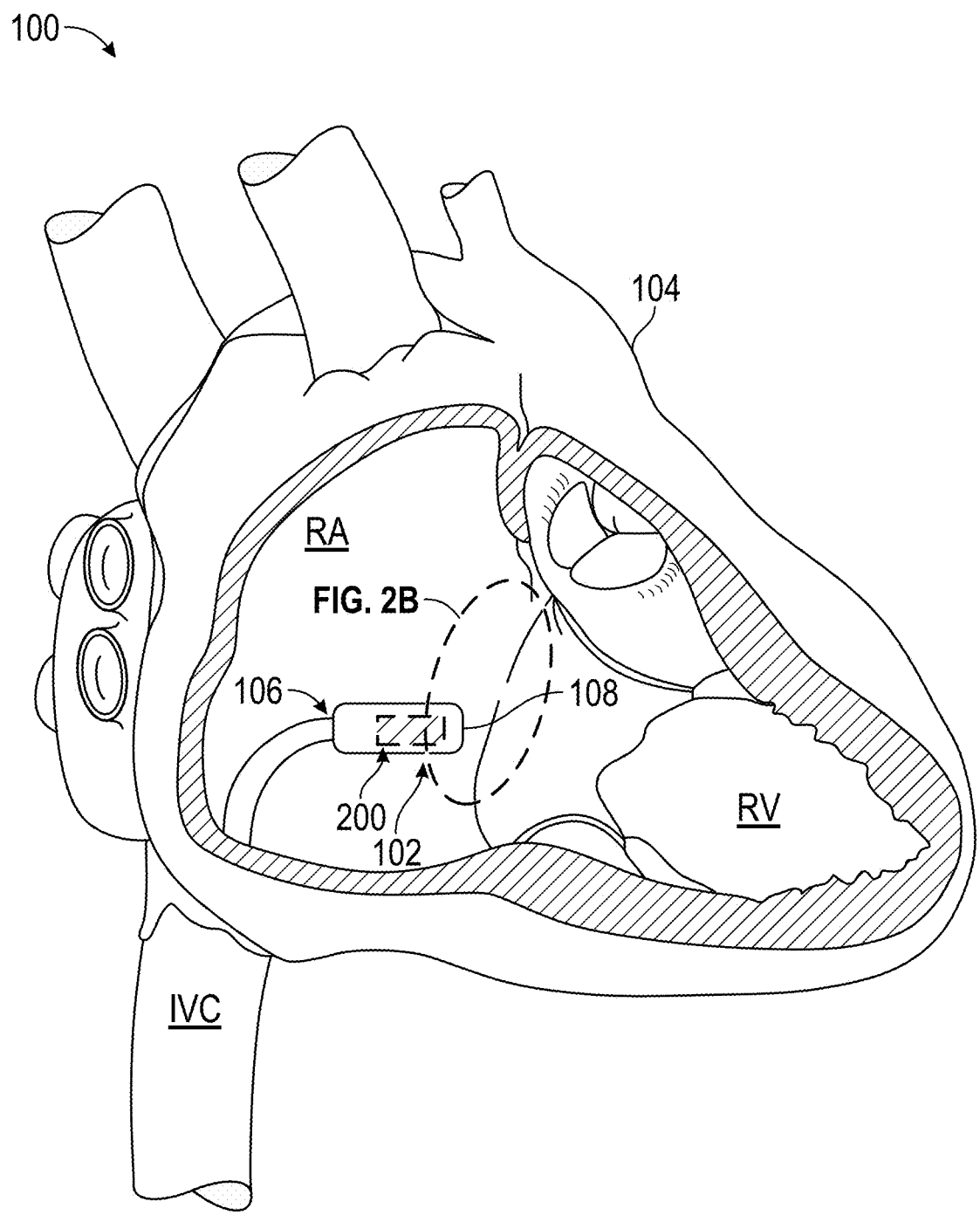
FIG. 1 is a conceptual diagram illustrating a portion of an example medical device system configured to implant a relatively compact implantable medical device at a target implant site.

This disclosure describes implantable medical devices (IMDs) that include a fixation component having a plurality of tines, components of such IMDs, medical device systems including such IMDs, and related techniques. An example IMD may include a housing and one or more elongate leadlets. The housing extends along a longitudinal axis from a proximal end of the housing to a distal end of the housing, and may enclose components of the IMD, such as circuitry and a battery. A first elongate leadlet extends from a proximal end of the leadlet to a distal end of the leadlet. The proximal end of the first leadlet is mounted to the housing, such as in proximity to the distal end of the housing. The distal end of the first leadlet may include an electrode, such as a first electrode of the IMD. The IMD may include additional electrodes, which may or may not be included as part of elongate leadlets extending from the housing of the IMD. The electrodes of the IMD may be configured to sense electrical signals from tissue and/or deliver electrical therapies to the tissue.

An example fixation component for the IMD may include a base and a plurality of tines. The base may define a longitudinal axis of the fixation component, and a proximal end and a distal end of the IMD may be aligned along the longitudinal axis. The longitudinal axis of the fixation component and IMD may be parallel and, in some cases, the fixation component and IMD may share a longitudinal axis. The base may be fixedly attached to the IMD near the distal end of the IMD. The plurality of tines may be spaced apart from one another around a perimeter of the distal end of the IMD and extend from the base. A shape of each respective tine of the plurality of tines may be selected to control deployment, tissue fixation, and/or tissue disengagement. For example, the shape of a respective tine may include a number of preset curves on the respective tine, a curvature (e.g., radius) of each preset curve on the respective tine, a length of each preset curve, a length of optional straight sections between preset curves, a width of the respective tine or sections thereof (e.g., one or more tapered portions), a thickness of the respective tine, a number of cutouts along the length of the respective tine, shapes of cutouts, or any combination thereof.

The plurality of tines may include a penetrator tine and a protector tine. When deployed, the plurality of tines may provide a desired tissue fixation. For example, the deformable preset curve of the penetrator tine and/or the protector tine may have a shape selected to penetrate tissue in a selected direction and a selected depth to fixate the IMD to the tissue. The deployed (e.g., undeformed) configuration of the penetrator tine and/or the protector tine may be selected to sufficiently fixate the IMD to selected tissue.

The IMD may be loaded into a delivery catheter by deforming the deformable preset curvature of the plurality of tines. When deployed at a target implant site, e.g., by allowing the tines to transition to the deployed configuration, the tines have a deployment stiffness that enables a respective tine to penetrate the tissue at a target implant site. By controlling the deployment stiffness, the tines may have improved tissue fixation, including control of a depth of tine penetration and an amount of tissue engagement in a lateral direction.

In some examples, the penetrator tine and protector tine may operate in conjunction with the first leadlet. The penetrator tine is configured to penetrate or cut a tissue to form a puncture in the tissue. The protector tine is configured to protect the first leadlet during deployment, such as, for example, by reducing an undesired displacement of the first leadlet or mechanical damage to the structure of the first leadlet. For example, during deployment from the delivery catheter, the penetrator tine may initially penetrate a selected tissue to form a puncture. Also, during deployment, the protector tine may urge the leadlet toward the penetrator tine, thereby guiding the leadlet and the protector tine into the puncture. As the fixation component is further deployed, the penetrator tine and protector tine may return from a deformed (e.g., pre-deployment) configuration to (or at least towards) the undeformed (e.g., deployed) configuration. When the penetrator and protector tines are in the deployed configuration, the first leadlet may extend in a distal direction between the penetrator tine and the protector tine, such that the first leadlet extends from the distal end of the housing of the IMD to reach a selected target tissue. In this way, the fixation component may provide improved electrode penetration to a selected depth within the selected tissue and improved electrode contact with the selected tissue.

After deployment at the target implant site, a deflection stiffness of the tines enables a clinician to confirm adequate fixation of the tines into tissue of a patient. For example, a pull test or a tug test may be performed under fluoroscopy to confirm that the tines have engaged the tissue to confirm adequacy of implantation of the 1 MB. The pull test or tug test may include the clinician pulling or tugging on the deployed IMD, e.g., via a tether coupled to a proximal end of the IMD, and observing movement of the tines to determine if the tines are engaged in tissue. For example, tines that are embedded in tissue may deflect or bend as the deployed IMD is pulled or tugged in the proximal direction. By controlling the deflection stiffness, the tines may have an improved flexibility that enables a clinician to more easily confirm tissue engagement.

In some examples, the plurality of tines may be configured to disengage from the tissue. For example, the IMD may be retrieved by a retrieval catheter. During retrieval, a retrieval member of the retrieval catheter may engage a proximal end of the IMD, such as a retrieval structure. The retrieval member may be withdrawn in a proximal direction into the retrieval catheter. When the retrieval catheter contacts the plurality of tines, the retrieval catheter may cause the plurality of tines to move from the undeformed configuration to the deformed configuration. By moving from the undeformed configuration to the deformed configuration during retrieval, the plurality of tines may improve tissue disengagement to facilitate extracting the IMD.

In some examples, the fixation component may include additional fixation tines. For example, the plurality of tines may further include at least one of one or more support tines, one or more guiding tines, or one of more deployment tines. In some examples, one or more support tines may be configured to engage selected tissue. In some examples, one or more guiding tines may be used to determine and/or control an orientation of the 1 MB during deployment. For example, the one or more guiding tines may include tines having a length greater than the other tines. The one or more guiding tines may be configured to provide a clinician with a visual indication, e.g., via fluoroscopy, of the orientation of the IMD prior to deployment of the penetrator tine and/or support tines. In some examples, one or more deployment tines may be configured to increase a deployment force of the IMD to, for example, improve tissue penetration of the penetrator tine and/or support tines.

In this disclosure, the example systems, devices, and techniques will be described with reference to delivering an IMD configured as a cardiac pacemaker to a target site in a heart of a patient. However, it will be understood that example systems, devices, and techniques of the present disclosure are not limited to delivering such IMDs to a target site in the heart. For example, the example systems, devices, and techniques described herein may be used to deliver other medical devices, such as drug delivery device, sensing devices, neurostimulation device, or medical electrical leads. Additionally, the example systems, devices, and techniques described herein may be used to deliver any such IMDs to other locations within a body of a patient. In short, the example systems, devices, and techniques described herein can find useful application in delivery of a wide variety of implantable medical devices for delivery of therapy to a patient or patient sensing.

FIG. 1 is a conceptual diagram illustrating a portion of an example medical device system 100 configured to implant a relatively compact implantable medical device 200 ("IMD 200") at a target implant site 102. In some examples, as illustrated in FIG. 1, the target implant site 102 may include an appendage of a right atrium (RA) of the heart 104 of a patient. In some examples, target implant site 102 may include other portions of heart 100 or other locations within a body of the patient. Medical device system 100 may include a delivery tool 106 configured to house and controllably deploy relatively compact IMD 200. In some examples, a clinician may maneuver medical device system 100 to target implant site 102. For example, with the IMD loaded therein, the clinician may guide delivery tool 106 up through the inferior vena cava IVC and into the RA. In some examples, other pathways or techniques may be used to guide delivery tool 106 into other target implant sites within the body of the patient.

Figure 2A:
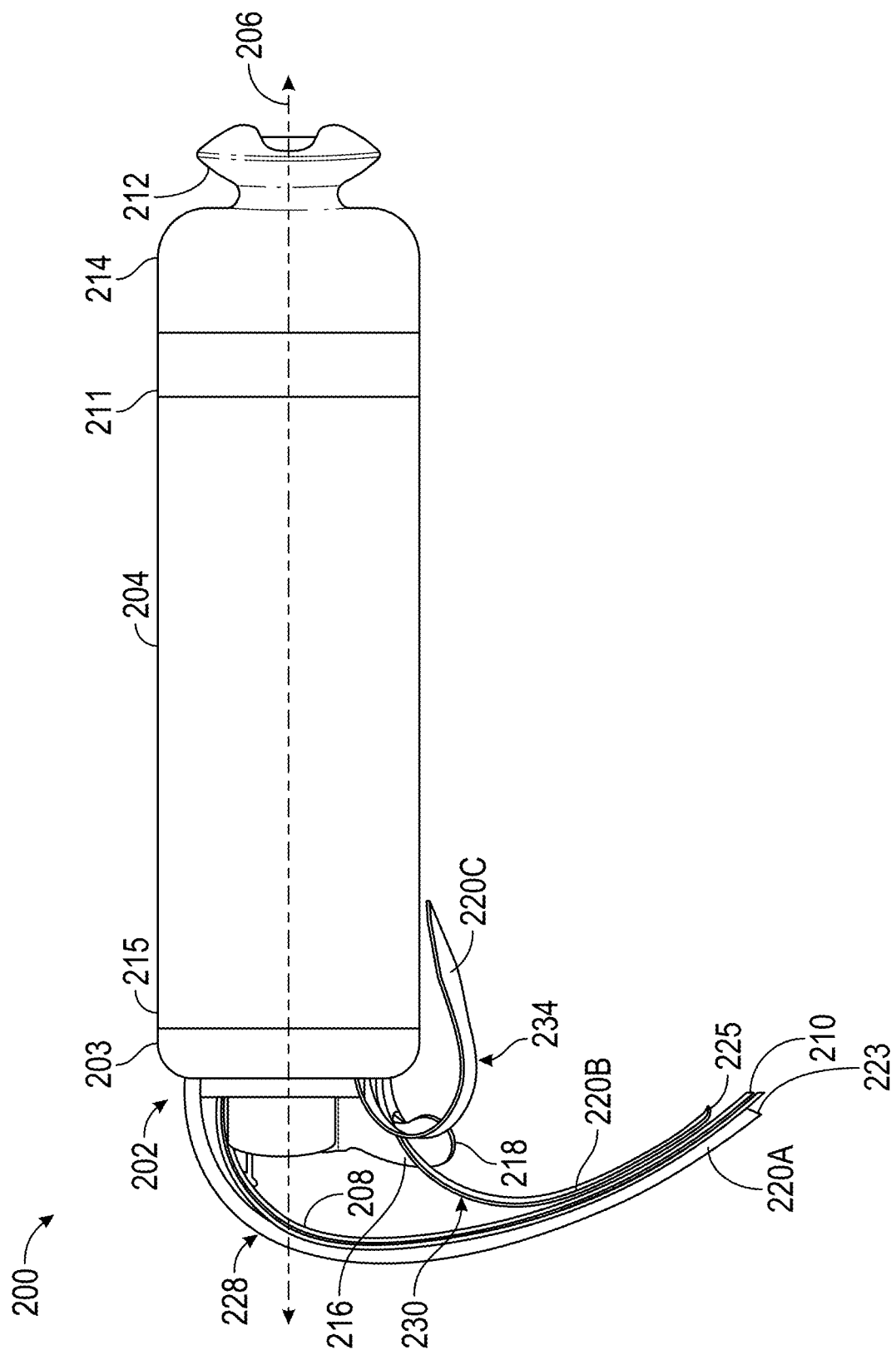
FIGS. 2A-2G are conceptual diagrams illustrating a relatively compact IMD including a fixation component.

FIG. 2A is a conceptual diagram illustrating a plan view of a relatively compact IMD 200 including a fixation component 202. IMD 200 includes housing 204 extending along longitudinal axis 206 from a proximal end 214 to a distal end 215. Housing 204 may be formed from a biocompatible and biostable metal such as titanium. In some examples, housing 204 may include a hermetically sealed housing. Housing 204 may include a nonconductive coating and define a return electrode 211 as an uncoated portion of housing 204. IMD 200 may include any suitable dimensions. In some examples, an outer diameter of IMD 200 (e.g., outer diameter of housing 204) may be between about 10 French (Fr) and about 30 Fr, such as about 20 Fr.

IMD 200 may contain electronic circuitry, including one or more of sensing circuitry (e.g., for sensing cardiac signals), therapy delivery circuitry (e.g., for generating cardiac pacing pulses), and processing circuitry for controlling the functionality of IMD 200, and may include a first leadlet 208. First leadlet 208 may terminate in a distal electrode 210. For example, leadlet 208 may include a conductor, such as an electrically conductive material, extending through a non-conductive jacket, such as polytetrafluoroethylene (PTFE) coating or polyether ether ketone (PEEK) tube, a portion of the conductor being exposed at electrode 210. The electronic circuitry may be configured to generate and deliver an electrical pulse therapy to tissue proximate leadlet 208 via first electrode 210, through the tissue to return electrode 211. Leadlet 208 may be spaced apart from distal end 215 of housing 204, for example, being coupled to the sensing and therapy delivery circuitry by the conductor of a hermetic feedthrough assembly (not shown).

In some examples, IMD 200 includes a retrieval structure 212 fixedly attached to proximal end 214 of housing 204. Retrieval structure 212 may be configured for temporarily tethering IMD 200 to a delivery catheter or a retrieval catheter, such as delivery tool 106. In some examples, retrieval structure 212 may be configured to couple to tether assemblies, such as those described in U.S. Patent Application No. 62/844,674, entitled "TETHER ASSEMBLIES FOR MEDICAL DEVICE DELIVERY SYSTEMS," the entire contents of which is incorporated herein by reference.

IMD 200 includes second leadlet 216. Second leadlet 216 may be similar to first leadlet 208 in at least some aspects. For example, second leadlet 216 may include a conductor, such as an electrically conductive material, extending through a non-conductive jacket, such as PTFE coating or a PEEK tube, a portion of the conductor being exposed at second electrode 218. First leadlet 208 may function in conjunction with second leadlet 216 for bipolar pacing and sensing, and/or first leadlet 208 and second leadlet 216 may each separately function with return electrode 211 for unipolar pacing and sensing of different selected tissues. In some examples, housing 204 may be overlaid with an insulative layer, for example, medical grade polyurethane, parylene, or silicone. In some examples, the insulative layer may define second electrode 218, for example, by removing a portion of the insulative layer to expose the metallic surface of housing 204. Second electrode 218 may be used with first leadlet 208 and/or second leadlet 216 for unipolar pacing and/or sensing.

Fixation component 202 includes a plurality of tines 220 ("tines 220"). Tines 220 may be configured to hold leadlets 208 and 216 in contact with tissue at a target implant site, e.g., target implant site 102. As illustrated in FIG. 2A, tines 202 include penetrator tine 220A, protector tine 220B, and support tine 220C. Tines 220 may include one or more sections. For example, tines 220 may include an elastically deformable material preset into one or more curved sections and one or more optional substantially straight sections. For example, penetrator tine 220A may include preset curvature 228, protector tine 220B may include preset curvature 230, and support tine 220C may include preset curvature 232. In some examples, tines 220 may define a ribbon shape configured to deform along a plane normal to longitudinal axis 206 and resist twisting outside of the plane. In some examples, tines 220 may include two or more curved sections (e.g., knuckles) as described in U.S. Patent Application No. 62/825,233, entitled "FIXATION COMPONENTS FOR IMPLANTABLE MEDICAL DEVICES," the entire contents of which is incorporated herein by reference. For example, support tine 220C may be the same or substantially similar to tines described in U.S. Patent Application No. 62/825,233.

Tines 220 may be configured to have a target deflection stiffness and a target deployment stiffness. The target deflection stiffness may include a measure of a resistance to force applied to IMD 200 in a proximal direction when fixation component 202 is engaged with tissue at target site 102. In some examples, the target deflection stiffness may be selected to enable tines 220 to deflect a predetermined amount to enable visualization of tines 220 under fluoroscopy. In some examples, the target deflection stiffness may be within a range from about 0.2 N to about 0.8 N, such as about 0.3 N to about 0.6 N. The deployment stiffness may include a measure of a force applied by tines 220 as tines 220 move from a deformed configuration to an undeformed configuration upon deployment of fixation component 202 from distal opening 108 of delivery tool 106 (FIG. 1) such that the free distal end of tines 202, (e.g., free distal end 352 penetrates pectinate muscle PM. In some examples, the target deployment stiffness may be within a range from about 0.6 N to about 1.2 N.

Figure 2B:
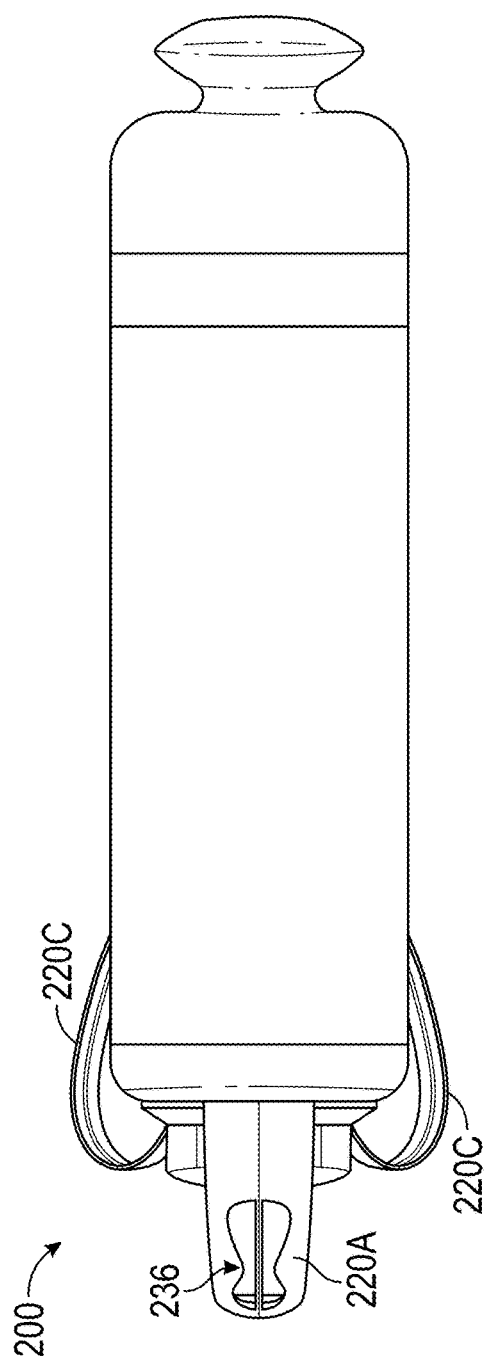
Figure 2C:
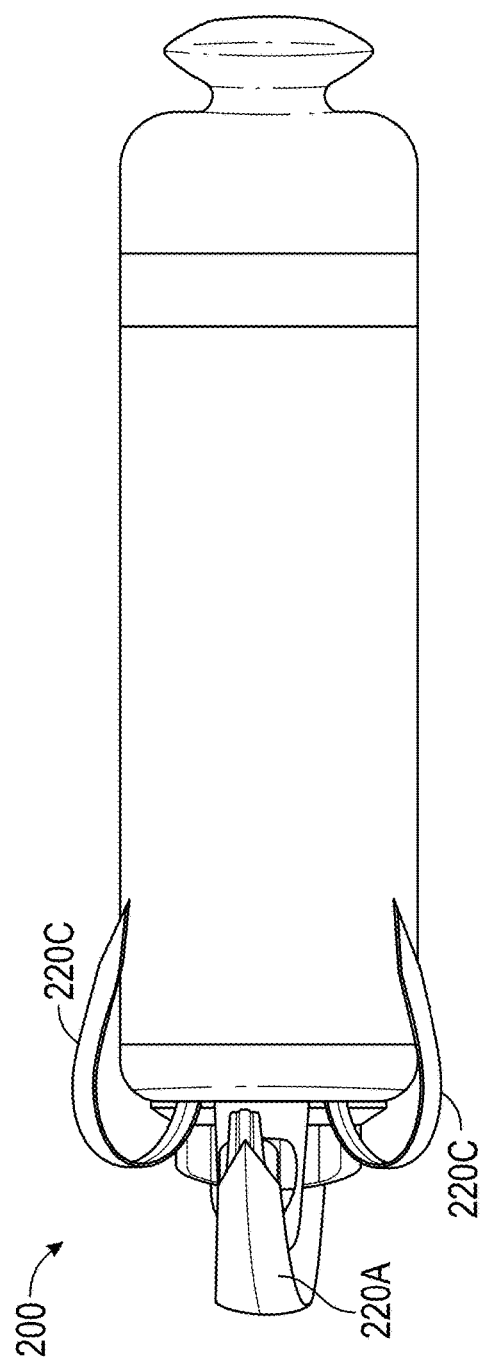
Figure 2E:
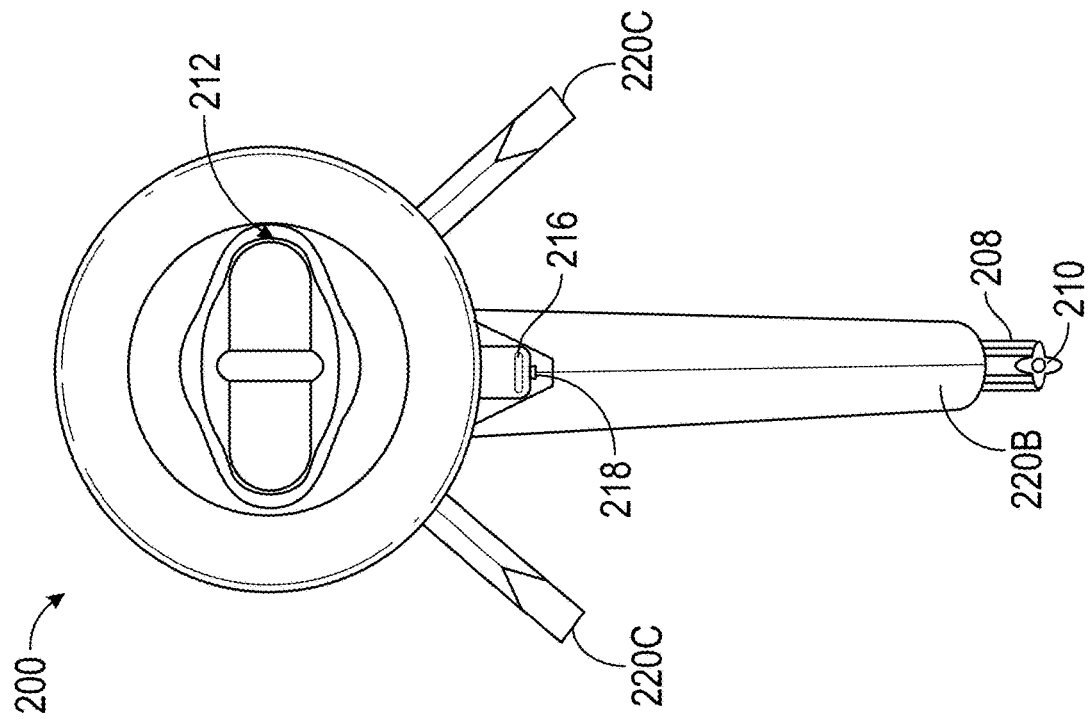
Figure 2D:
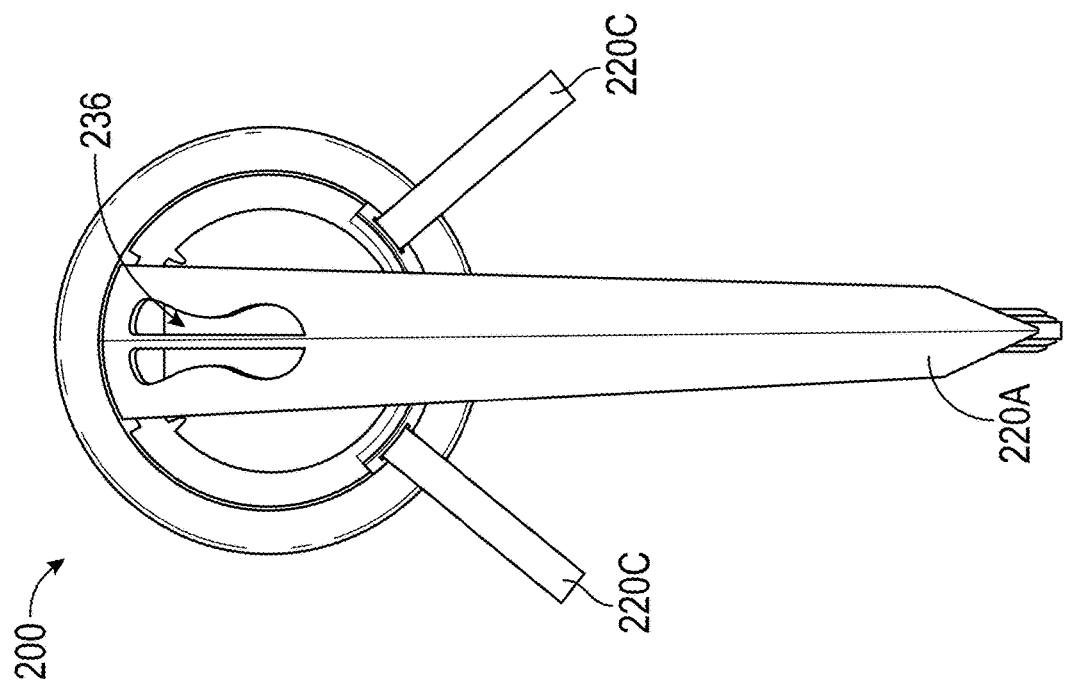
Figure 2F:
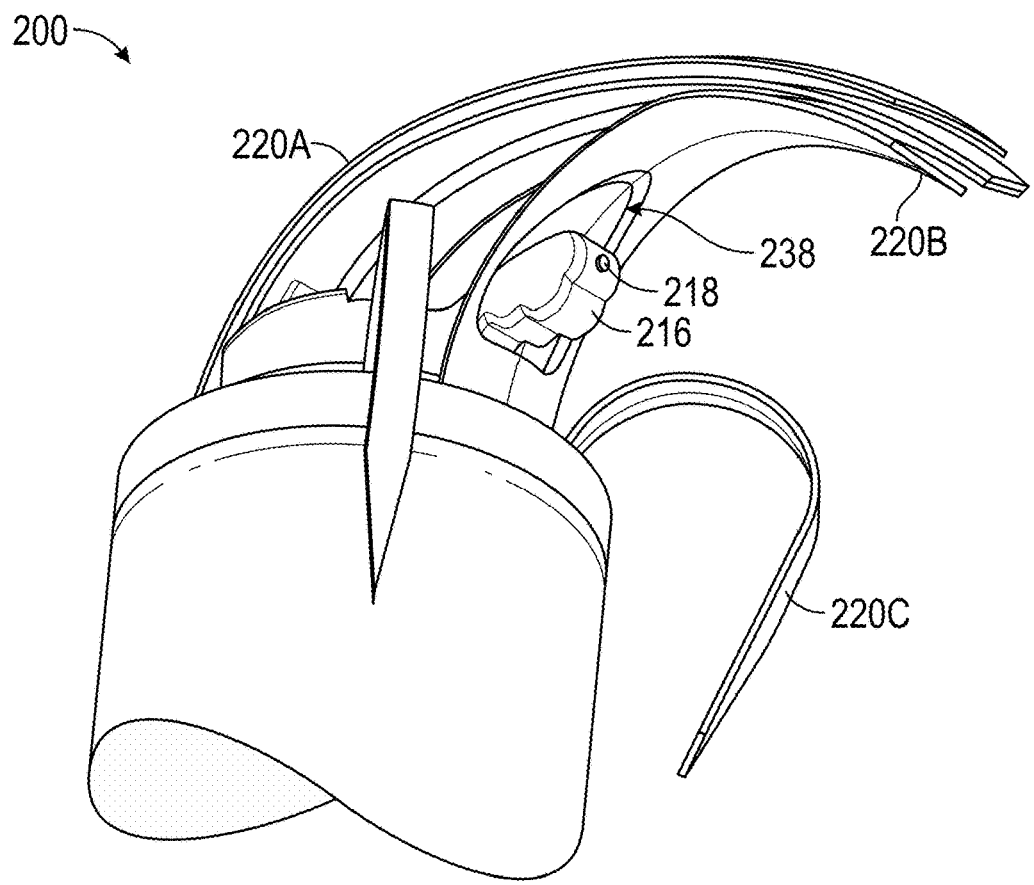
Figure 2G:
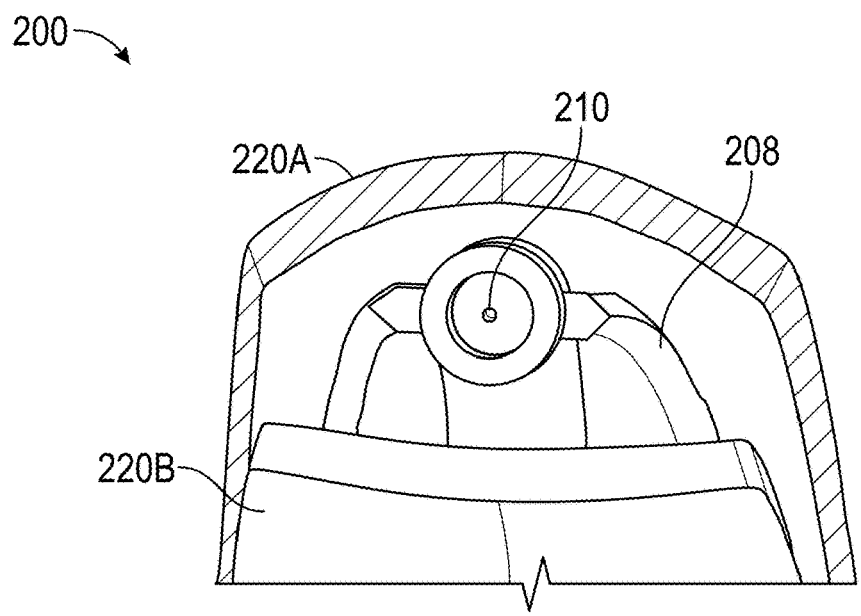

FIGS. 2B-2F illustrate different views of IMD 200. In some examples, as illustrated in FIGS. 2B and 2D, penetrator tine 220A may define an aperture 236. Aperture 236 may be configured to control a deployment stiffness or deflection stiffness of penetrator tine 220A. For example, aperture 236 may define a shear stress reduction region configured to reduce shear stress in penetrator tine 220A when bent, such as when bent into the deformed configuration or during a pull test or tug test. In some examples, at least a portion of first leadlet 208 may extend though aperture 236. By extending through aperture 236, first leadlet 208 may be adjustable. For example, a delivery catheter member may be configured to, before or after deployment of IMD 200, grasp the portion of first leadlet 208 extending through aperture 236. After deployment of IMD 200, the delivery catheter may be used to adjust an amount of the portion of first leadlet 208 extending through aperture 236 to control an amount of leadlet 208 extending beyond distal end 223 of penetrator tine 220A or a distal end 225 of protector tine 220B. In some examples, penetrator tine 220A may include other features configured to control a deployment stiffness or deflection stiffness of penetrator tine 220A or interact with other components of IMD 200. For example, penetrator tine 220A may define additional apertures or one or more grooves configured to control a deployment stiffness or deflection stiffness of penetrator tine 220A or in which first leadlet 208 may move in sliding engagement during deployment.

In some examples, as illustrated in FIG. 2E, protector tine 220B may define an aperture 238. Protector tine 220B and second leadlet 216 may be configured such that at least second electrode 218 may protrude through aperture 238 when in the deployed configuration. For example, protector tine 220B may define additional apertures or one or more grooves configured to control a deployment stiffness or deflection stiffness of protector tine 220B or in which second leadlet 216 may move in sliding engagement during deployment.

Figure 3:
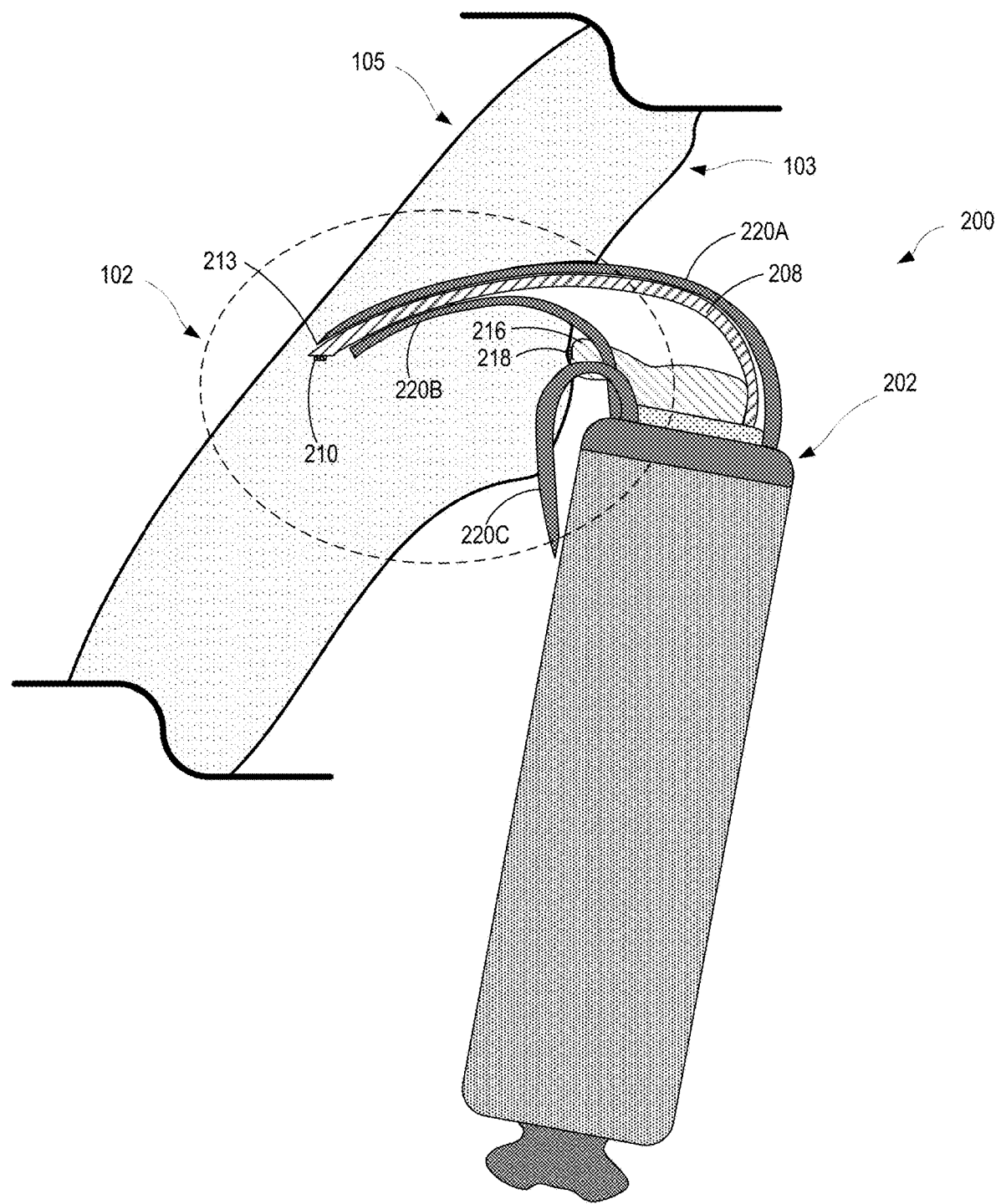
FIG. 3 is a conceptual diagram illustrating the example IMD illustrated in FIGS. 2A-2G implanted at an example target implant site.

FIG. 3 is a conceptual diagram illustrating IMD 200 implanted at target implant site 102. Tines 220 may define a deformable preset curvature configured to position leadlets 208 and 216 at selected tissue of a target implant site 102. Target implant site 102 includes a portion the right atrial RA wall, such as the atrioventricular septum having an atrial surface 103 and a ventricular surface 105. In other examples, target implant site 102 may include other tissues within a body of a patient. When deployed at target implant site 102, tines 220 have a deployment stiffness that enables a respective tine to penetrate selected tissue at target implant site 102. For example, IMD 200 may be secured at target implant site 102 by tines 220 of fixation component 202 penetrating through the myocardium, such as a layer of pectinate muscle. Tines 220 are configured for spring-loaded release, upon deployment out through distal opening 108 of delivery tool 106 (FIG. 1) such that free distal end of tines 202 (e.g., free distal end 223 of penetrator tine) penetrates the myocardium. It should be noted that alternate suitable implant sites for fixation component 202 can be along any suitable surface of the heart or other tissue within a body of a patient. By controlling the deployment stiffness, tines 220 may have improved tissue fixation, including control of a depth of penetration and an amount of tissue engagement in a lateral direction.

Figure 4A:
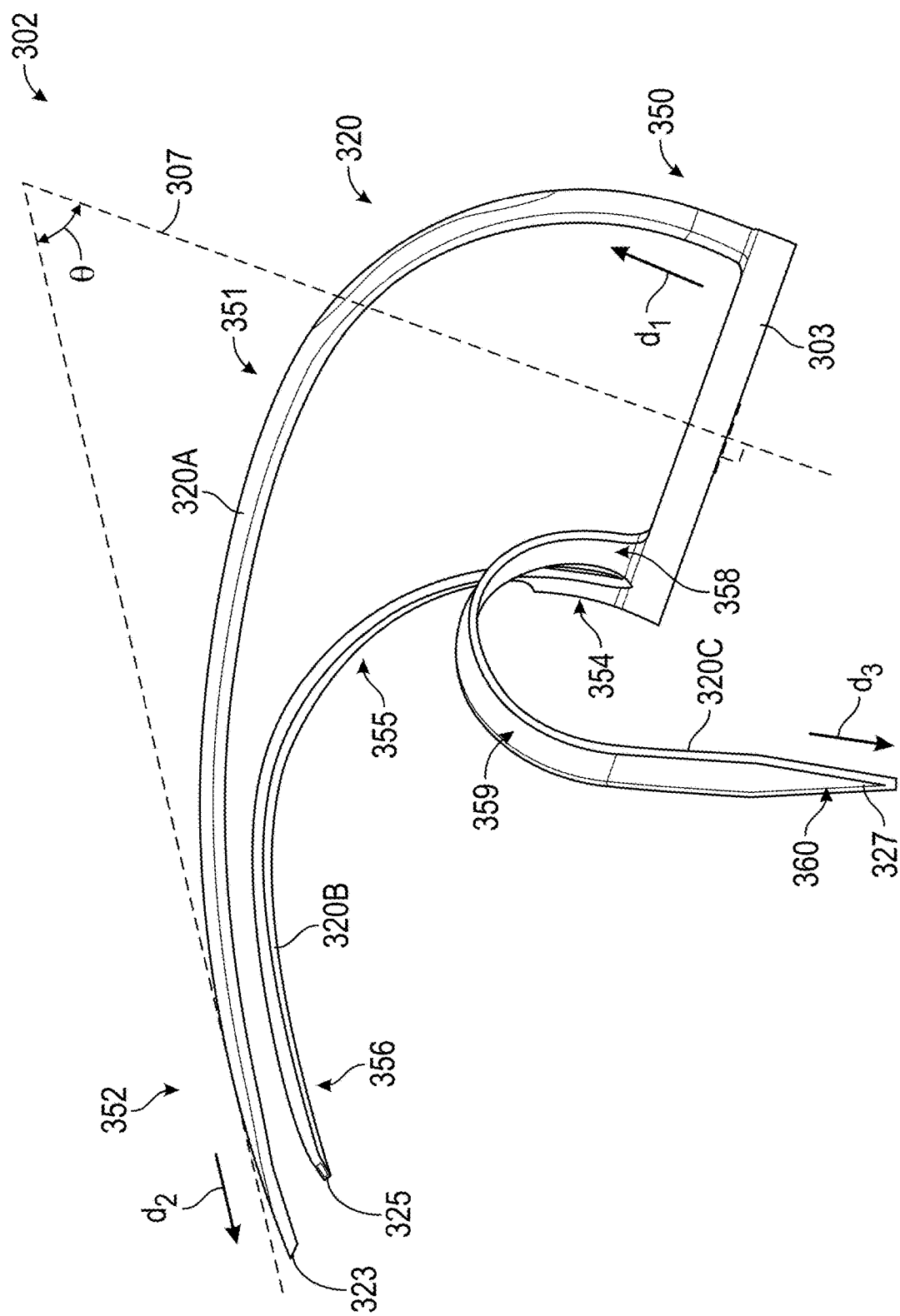
FIGS. 4A and 4B are conceptual diagrams illustrating an example fixation component.
Figure 4B:
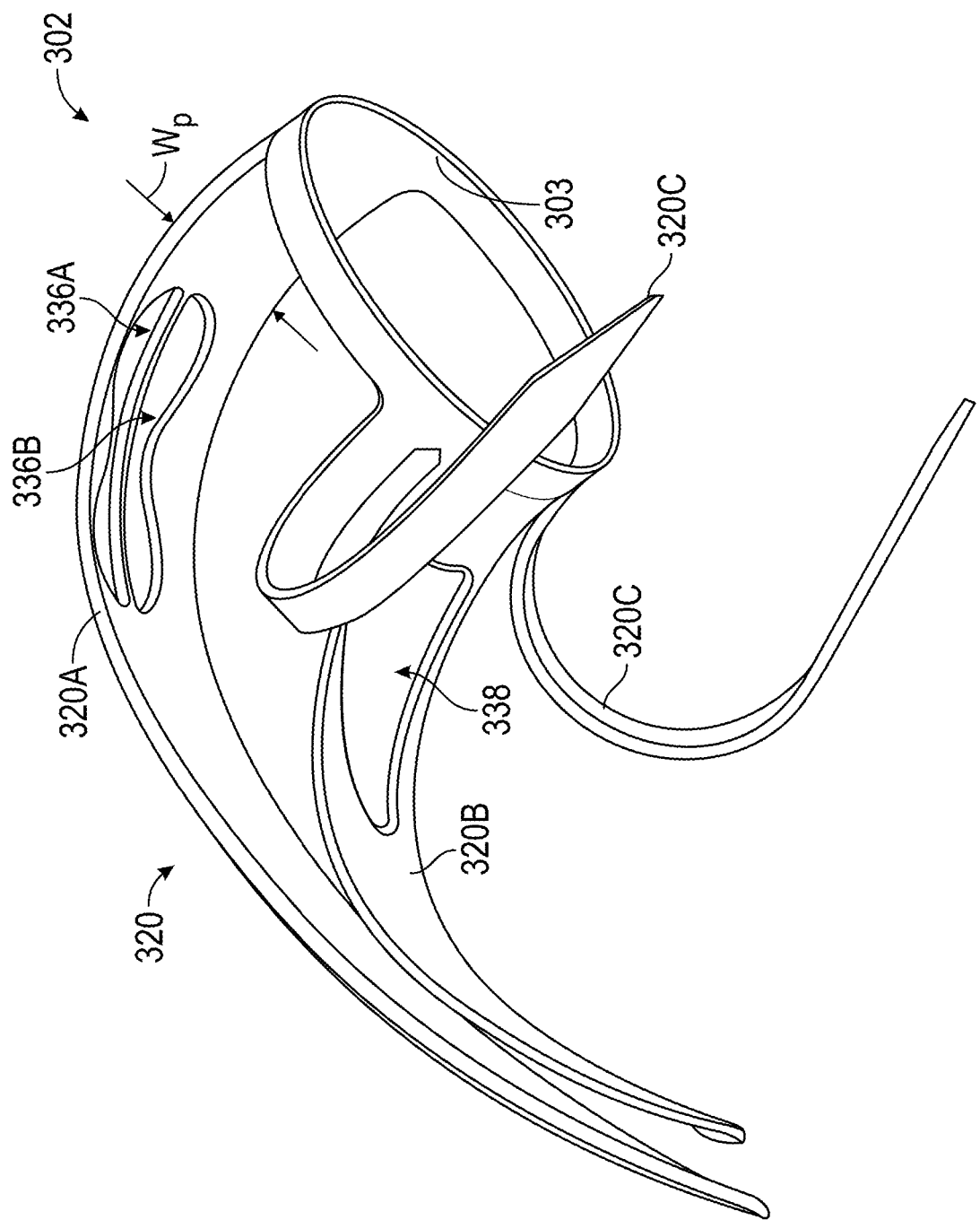

FIGS. 4A and 4B are conceptual diagrams illustrating an example fixation component 300. Fixation component 302 may be the same as or substantially similar to fixation component 202, except for the differences described herein. For example, fixation component 302 includes tines 320. Tines 320 are illustrated in a deployed (e.g., undeformed) configuration.

Fixation component 302 includes base 303. Base 303 may define a longitudinal axis 307 of fixation component 302. When base 303 is mounted around distal end 215 of device housing 204 such that a perimeter of fixation component 302 extends around housing 204, longitudinal axis 307 is generally aligned along longitudinal axis 206 of IMD 200 (FIG. 2A).

As illustrated in FIG. 4B, tines 320 are spaced apart from one another around a perimeter of base 303. Base 303 may have any suitable inner diameter and outer diameter. In some examples, base 303 may have an inner diameter within a range from about 0.1 inch (2.54 millimeters, mm) to about 0.3 inch (7.62 mm), such as 0.20 inch (5.08 mm), and an outer diameter within a range from about 0.11 inch (2.794 mm) to about 0.31 inch (7.874 mm), such as about 0.21 inch (5.334 mm). In some examples, fixation component 302 may be mounted to distal end 202 of device housing 204, for example, in a manner the same or substantially similar to that described in U.S. Pat. No. 10,099,050B2 (filed on Jan. 19, 2017), which is incorporated herein by reference in its entirety. In some examples, fixation component 302 may include separately formed tines 320 that are individually mounted to distal end 202 of device housing 204 (e.g., not integrated together with base 303).

Tines 320 may include any suitable elastically deformable biocompatible material. In some examples, tines 320 may include a super-elastic material, such as, for example, a nickel-titanium alloy. For example, fixation component 302 may be cut from a medical grade nickel-titanium alloy tubing that conforms to the chemical, physical, mechanical, and metallurgical requirements of the ASTM F2063 standard, and has a wall thickness of about 0.005 inch (0.127 mm). In this way, tines 320 may be integrally formed with base 303 and each tine of tines 320 may have a constant thickness "t" of about 0.005 inch±0.001 inch (0.127 mm±0.0254 mm). In some examples, after cutting the tubing or otherwise forming fixation component 302, tines 320 may be shaped into a preset configuration by bending and holding tines 320, while heat treating according to methods known to those skilled in the art.

As illustrated in FIG. 4A, penetrator tine 320A may include proximal section 350, curved section 351, and distal section 352. Each of proximal section 350, curved section 351, and distal section 352 may include any suitable length. In some examples, a length of penetrator tine 320A may be within a range from about 2 mm to about 15 mm, such as from about 4 mm to about 10 mm. Proximal section 350 is fixedly attached to base 303. Proximal section 350 extends in a first direction $d_1$. In some examples, first direction $d_1$ may be substantially parallel to longitudinal axis 307. In some examples, first direction $d_1$ may be at an angle relative to longitudinal axis 307, such as for example, between about 0 degrees to about 5 degrees. Curved section 351 may include a deformable preset curvature. Curved section 351 extends from proximal section 350 laterally across longitudinal axis 307 to distal section 352. In some examples, curved section 351 may include a single radius within a range from about 0.06 inch (1.520 B mm) to about 0.08 inch (2.032 mm), such as about 0.067 inch±0.010 inch (1.7018 mm±0.254 mm). In some examples, curved section 351 may include more than one curved section.

Distal section 352 may include a substantially straight segment that terminates in distal end 323. Distal end 323 of penetrator tine 320A may include an incisive shape. In some examples, the incisive shape may include a shape tapering to a point or an edge that is sufficiently small to pierce a tissue or cut a tissue. In some examples, an incisive shape may include a pointed shape, such as a needle shape. In some examples, an incisive shape may include a blade shape that tapers to a sharp edge, a tanto tip, a forked tip, a dual tanto forked tip, or a dual tanto forked tip with curved cutting surface. In some examples, the shape of distal end 323 of penetrator tine 320A may be based, at least in part, on a deployment force of penetrator tine 320A. For example, penetrator tine 320A having a lesser deployment force may require a sharper distal end 323 to achieve penetration of a tissue, compared to a penetrator tine 320A having a greater deployment force which may have a relatively less sharp distal end 323 to achieve penetration of a tissue. In this way, the selected shape of distal end 223 may improve tissue penetration, reduce a deployment force required to penetrate tissue, and/or better control tissue penetration depth compared to other distal ends.

Distal section 352 may be oriented by curved section 351 such that distal section 352 substantially extends, within manufacturing limits, in direction $d_2$. In some examples, the angle $\theta$ between $d_1$ and $d_2$ may be within a range between about 35 degrees and 145 degrees relative to longitudinal axis 307, such as about 90 degree or about 135 degrees.

Protector tine 320B may include proximal section 354, curved section 355, and distal section 356. Each of proximal section 354, curved section 355, and distal section 356 may include any suitable length. Proximal section 354 is fixedly attached to base 303. Proximal section 354 extends in a first direction $d_1$, as discussed above. Curved section 355 may include a deformable preset curvature. Curved section 355 extends from proximal section 354 laterally, outward from longitudinal axis 307 to distal section 356. In some examples, curved section 355 may include a single radius within a range from about 0.06 inch (1.520 B mm) to about 0.08 inch (2.032 mm), such as about 0.067 inch±0.010 inch (1.7018 mm±0.254 mm). In some examples, curved section 355 may include more than one curved section. Distal section 356 may include a substantially straight segment that terminates in distal end 325. Distal end 325 of protector tine 323 may include any suitable shape, such as, for example, a rounded shape or an incisive shape. Distal section 356 may be oriented by curved section 355 such that distal section 356 substantially extends in direction $d_2$, as discussed above.

Support tine 320C may include proximal section 358, curved section 359, and distal section 360. Each of proximal section 358, curved section 359, and distal section 360 may include any suitable length. Proximal section 358 is fixedly attached to base 303. Proximal section 358 extends in a first direction $d_1$, as discussed above. Curved section 359 may include a deformable preset curvature. Curved section 359 extends from proximal section 358 laterally, outward from longitudinal axis 307 to distal section 360. In some examples, curved section 355 may include a single radius within a range from about 0.06 inch (1.520 B mm) to about 0.08 inch (2.032 mm), such as about 0.067 inch±0.010 inch (1.7018 mm±0.254 mm). In some examples, curved section 355 may include more than one curved section. Distal section 360 may include a substantially straight segment that terminates in distal end 327. Distal end 327 of support tine 320C may include any suitable shape, such as, for example, a rounded shape or an incisive shape. Distal section 360 may be oriented by curved section 359 such that distal section 360 substantially extends, within manufacturing limits, in direction $d_3$.

The shape (e.g., deformable preset curve) and width of each tine of tines 320, and, in some examples, the superelastic stiffness properties of nickel-titanium alloy, provide a sufficient spring force and structural stiffness for tines 320 to engage tissue for the fixation of IMD 200 at an implant site when deployed by delivery tool 106, as described in greater detail below. For example, with reference to FIG. 4B, penetrator tine 320A has a proximal width "$W_P$" in a range from about 0.020 inch (0.508 mm) to about 0.1 inch (2.54 mm), such as about 0.06 inch (1.520 B mm). In some examples, tines 320 may have a substantially constant width (e.g., constant or nearly constant within the limits of common manufacturing tolerances) along the length of tines 320. For example, proximal section 358, curved section 359, and distal section 360 of support tine 320C may have a substantially constant width. In some examples, a width of tines 320 may taper toward a respective distal end. For example, a width of penetrator tine 320A may taper from about 0.1 inch (2.54 mm) at a proximal width $W_P$ to about 0.024 inch (0.6 mm) at a distal width. In some examples, the taper of penetrator tine 320A may be selected and shaped to provide tissue penetration up to a selected width of the taper. For example, penetrator tine 320A may taper from about 0.59 inch (1.5 mm) at a proximal width $W_P$ to about 0.020 inch (0.508 mm) at a distal width and be configured to penetrate tissue up to about a width of 0.028 inch (0.7 mm). In some examples, a tapered portion of a respective tine of tines 320 may include a plurality of tapers, each taper having a respective maximum width and respective minimum width. Generally, a tapered portion may increase the flexibility of a respective tine relative to an untampered portion. In this way, one or more tapers may be used to selectively control a deployment stiffness, a deflection stiffness, and/or a tissue penetration depth. In some examples, a width of tines 220 may be selected to provide a radiopaque density that facilitates fluoroscopic visualization during and after the implant procedure.

In some examples, rather than tapered portions, tines 320 may include cutouts, engravings, embossing, or other variations in the thickness of tines 320. For example, penetrator tine 320A include apertures 336A and 336B. Apertures 336A and 336B may include any suitable shape, length, and/or width. Similarly, protector tine 320B may include aperture 338. In some examples, cutouts, engravings, embossing, or other variations in the thickness of tines 320 may be configured to increase the flexibility of a selected portion of tines 320 relative to other portions of tines 320. For example, apertures 336A and 336B may increase a flexibility of curved section 351 of penetrator tine 320A. By increasing the flexibility of the selected portion of a respective tine of tines 320, the respective tine may have, after forming the preset curvature, a reduced deployment stiffness and/or deflection stiffness compared to a tine without cutouts, engravings, embossing, or other variations in the thickness.

In some examples, the tines of a fixation component may include more than two curved sections to result in a target deflection stiffness and a target deployment stiffness. FIGS. 5A-5D are conceptual diagrams illustrating an example fixation component 502 that includes a protector tine 520B having a plurality of curved sections. Fixation component 502 may be the same as or substantially similar to fixation components 202 and/or 302 discussed above in reference to FIGS. 2A-4B, except for the differences describe herein. For example, fixation component 502 includes base 503 from which tines 520 extend and are spaced apart from one another around a perimeter of base 503. Base 503 may define a longitudinal axis 507 of fixation component 502, which may, in some examples, generally aligned along longitudinal axis 206 of IMD 200 (FIG. 2A). Penetrator tine 520A and protector tine 520B extend laterally, outward from longitudinal axis 507 at an angle θ of about 45 degrees.

Figure 5A:
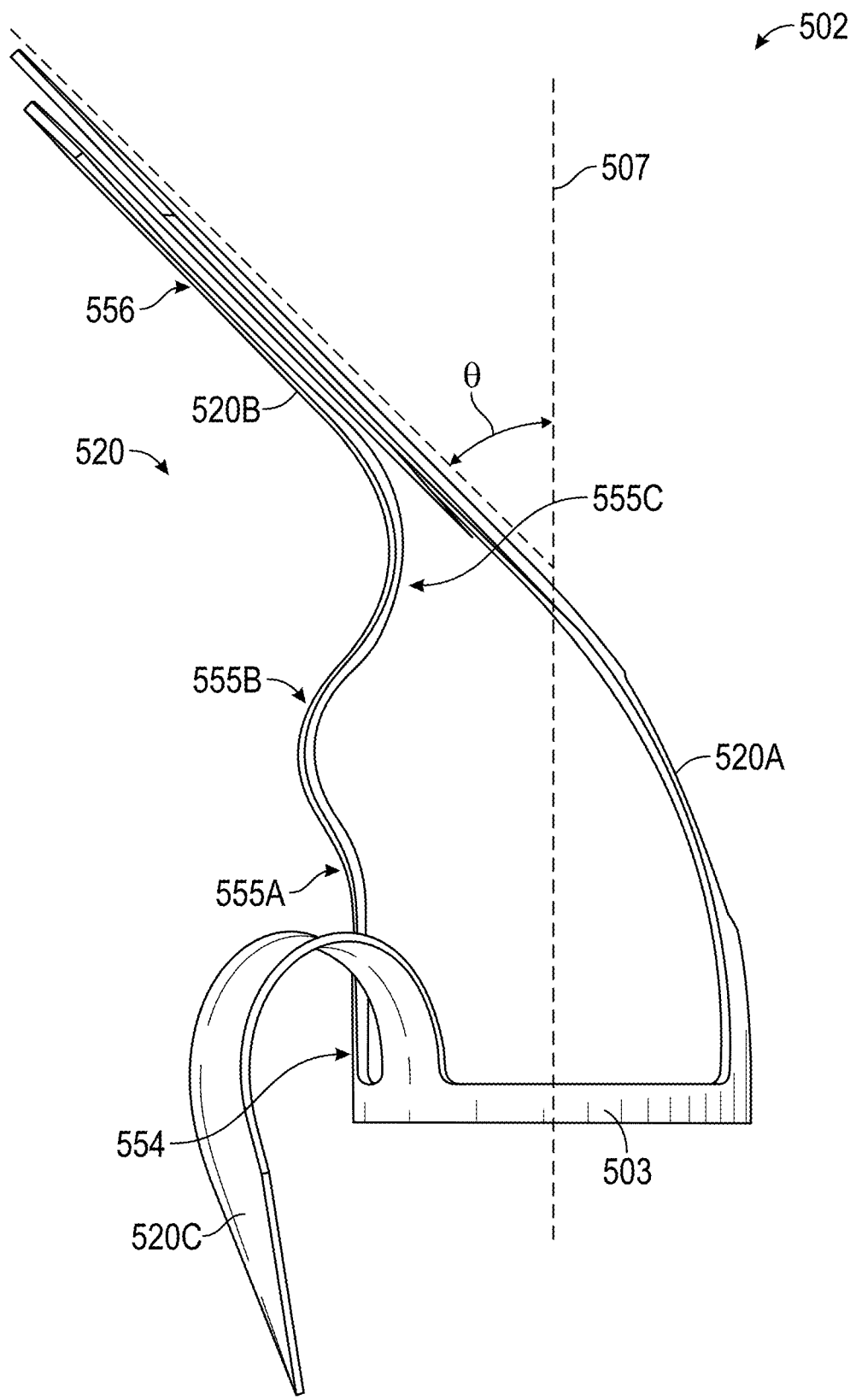
FIGS. 5A-5D are conceptual diagrams illustrating an example fixation component that includes a protector tine having a plurality of curved sections.

As illustrated in FIG. 5A, protector tine 520B includes proximal section 554, first curved section 555A, second curve section 555B, third curve section 555C, and distal section 556. Proximal section 520B is fixedly attached to base 503. Each of proximal section 554, first curved section 555A, second curve section 555B, third curve section 555C, and distal section 556 may be sized and shaped to enable protector tine 520B to have a target deflection stiffness and/or a target deployment stiffness.

First curved section 555A, second curve section 555B, and third curve section 555C may include respective deformable preset curvatures. For example, first curved section 555A extends from proximal section 554 laterally, outward from longitudinal axis 507 to second curved section 555B. In some examples, first curved section 555A may include a single radius within a range from about 0.02 inch (0.508 mm) to about 0.08 inch (2.032 mm), such as 0.06 inch (1.520 B mm). Second curved section 555B extends from first curved section 555A laterally toward longitudinal axis 507 to third curved section 555C. In some examples, second curved section 555B may include a single radius within a range from about 0.02 inch (0.508 mm) to about 0.08 inch (2.032 mm), such as 0.06 inch (1.520 B mm). Third curved section 555C extends from second curved section 555B laterally, outward from longitudinal axis 507 to distal section 556. In some examples, third curved section 555C may include a single radius within a range from about 0.02 inch (0.508 mm) to about 0.1 inch (2.54 mm), such as 0.08 inch (2.032 mm).

In some examples, protector tine 520B may further include one or more straight sections between first curved section 555A and second curve section 555B or second curved section 555B and third curve section 555C. The one or more straight sections may include a length within a range from about 0.01 inch (0.254 mm) to about 0.1 inch (2.54 mm).

Figure 5B:
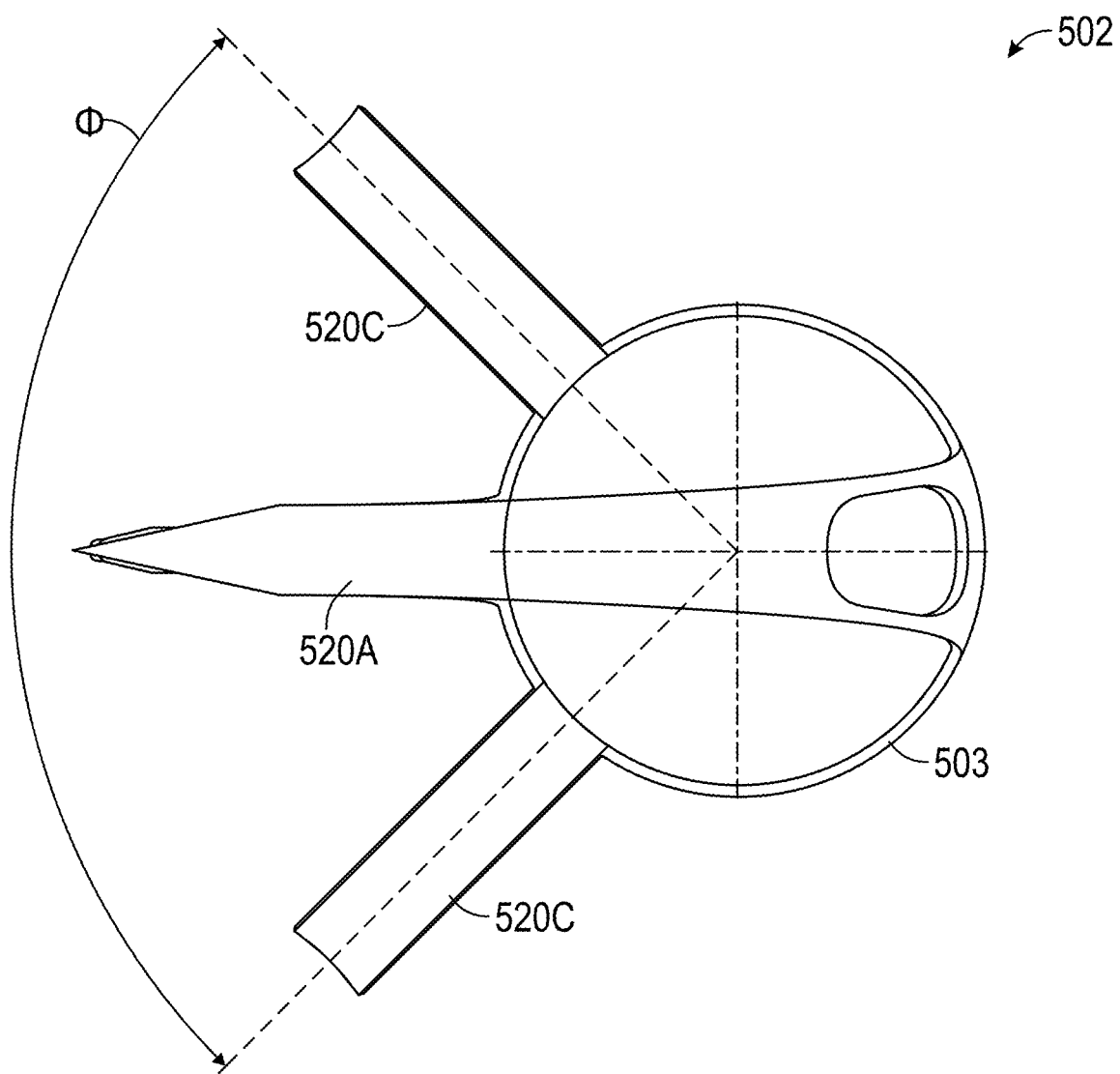
Figure 5C:
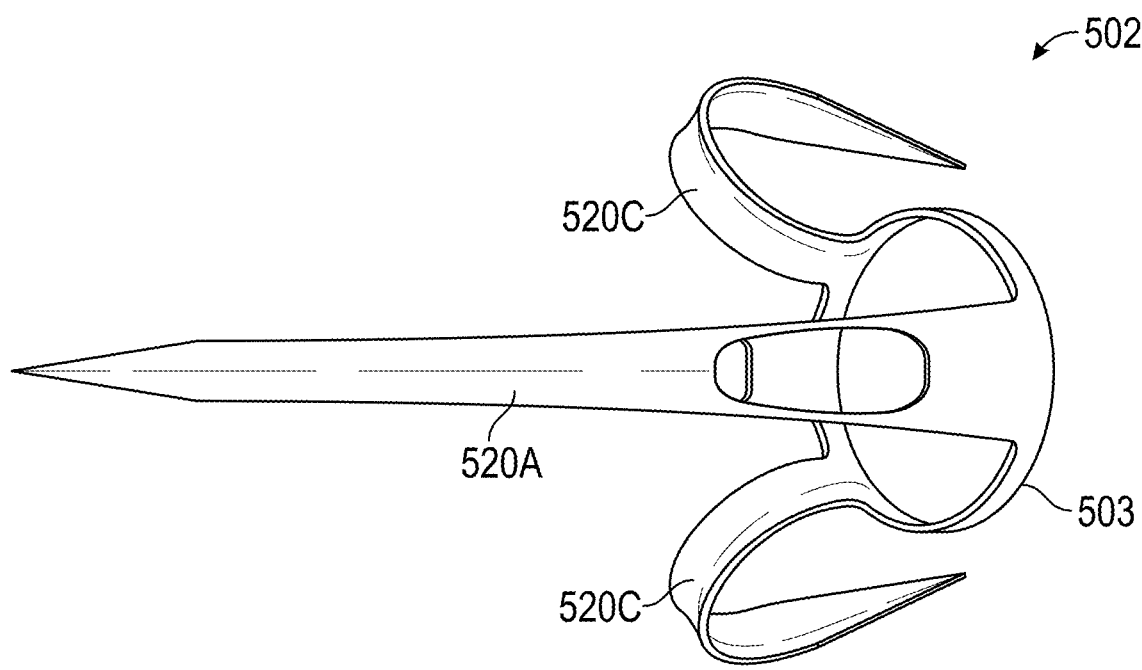
Figure 5D:
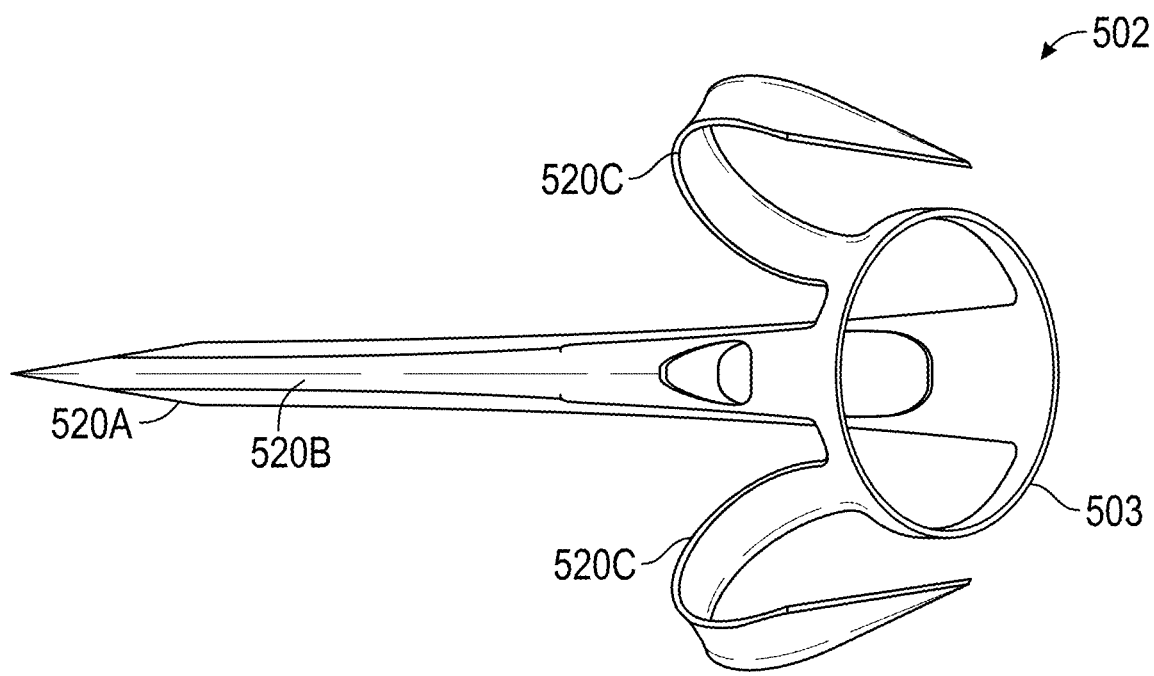

As illustrated in FIG. 5B, tines 520 are spaced apart from one another around a perimeter of base 503. In some examples, support tines 520C may be spaced apart relative to one another at any suitable angle Φ, such as an angle within a range from about 60 degrees to 120 degrees, such as 90 degrees. In some examples, a spacing of support tines 520C about 45 degrees from protector tine 520B, e.g., 90 degrees relative to one another, may improve fixation of an IMD (e.g., IMD 200) by increasing an amount of tissue engaged by support tines 520C if penetrator tine 520A and protector tine 520B are off-perpendicular relative to a selected tissue at a target implant site.

Figure 6:
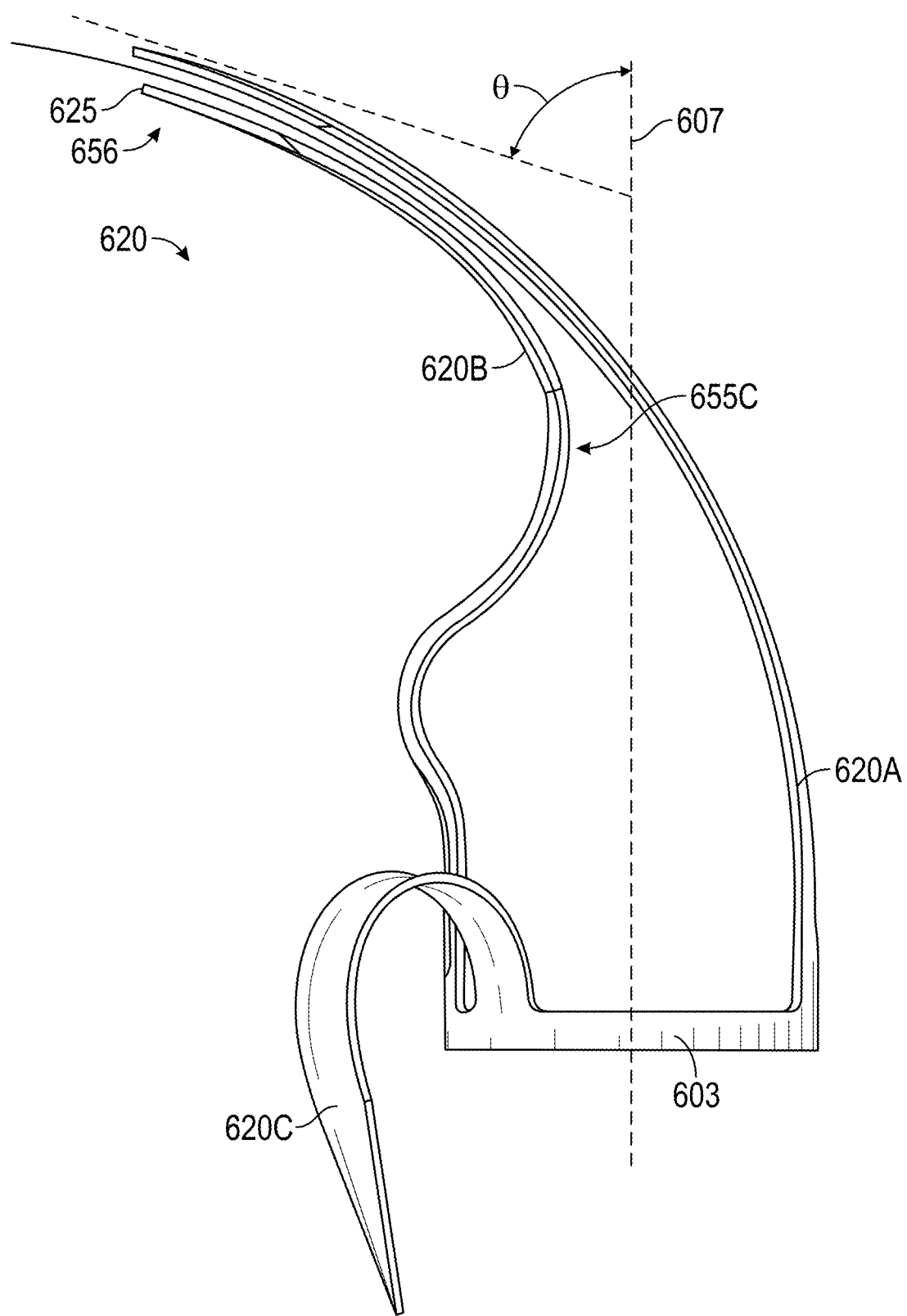
FIG. 6 is a conceptual diagram illustrating an example fixation component that includes a protector tine having a plurality of curved sections.

In some examples, a respective curved section extends to, or nearly to, a respective distal end of a respective tine. FIG. 6 is a conceptual diagram illustrating an example fixation component 602 that includes a protector tine 620A having a plurality of curved sections. Fixation component 602 may be the same as or substantially similar to fixation components 202, 302, and/or 502 discussed above in reference to FIGS. 2A-5D, except for the differences describe herein. For example, fixation component 602 includes base 603 from which tines 620 extend and are spaced apart from one another around a perimeter of base 603. Base 603 may define a longitudinal axis 607 of fixation component 602, which may, in some examples, generally aligned along longitudinal axis 206 of IMD 200 (FIG. 2A). Penetrator tine 620A and protector tine 620B extend laterally, outward from longitudinal axis 607 at an angle θ of about 80 degrees. Additionally, third curved section 655C of protector tine 620C extends to distal section 656 nearly at distal end 625.

Figure 7B:
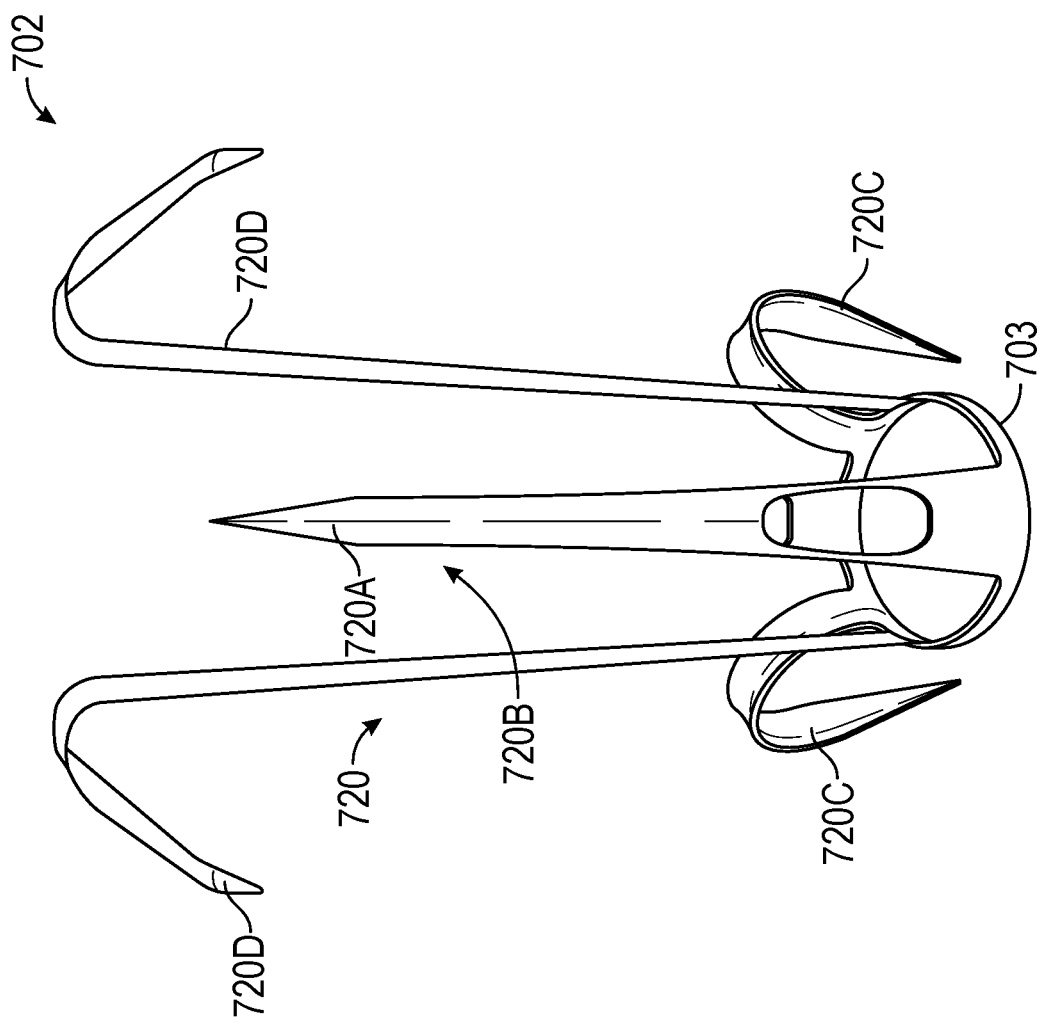
FIGS. 7A and 7B are conceptual diagrams illustrating an example fixation component that includes guiding tines.
Figure 7A:
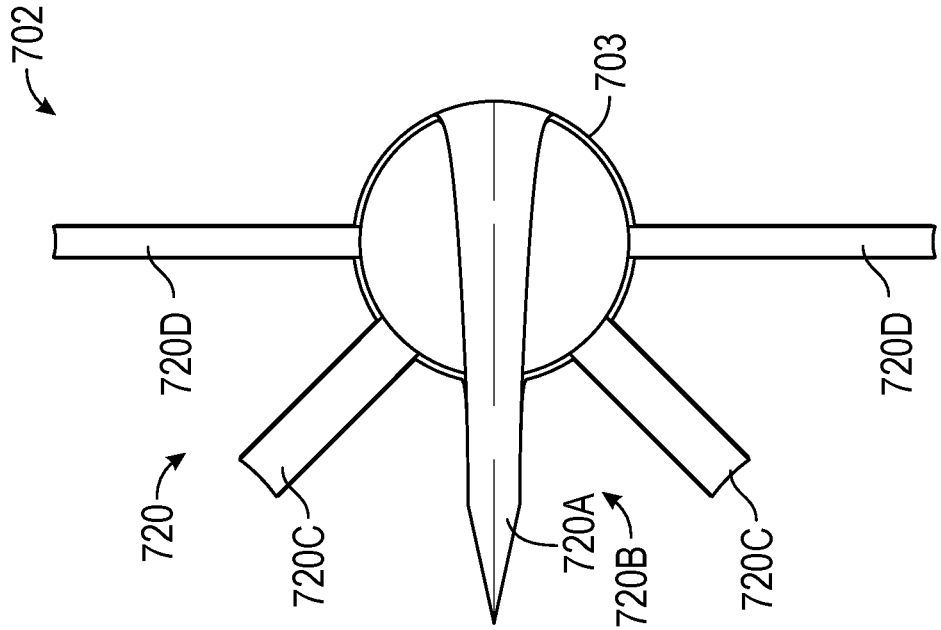

In some examples, a fixation component may include one or more guiding tines. FIGS. 7A and 7B are conceptual diagrams illustrating an example fixation component 702 that includes guiding tines 720D. Fixation component 702 may be the same as or substantially similar to fixation components 202, 302, 502, and/or 602 discussed above in reference to FIGS. 2A-6, except for the differences describe herein. For example, fixation component 702 includes base 703 from which tines 720 extend. Tines 720 include penetrator tine 720A, protector tine 720B, support tines 720C, and guiding tines 720D. Guiding tines 720D may be spaced apart from protector tine 720B an angle within a range from about 80 degrees to about 90 degrees. In some examples, guiding tines 720D may include non-incisive distal ends. In some examples, guiding tines 720D may be used to determine and/or control an orientation of an IMD (e.g., IMD 200) during deployment. For example, guiding tines 720D may have a length greater than the other tines, e.g., penetrator tine 720B. During deployment, guiding tines 720D may extend out of distal opening 108 of delivery catheter 106 before the other tines. In this way, a clinician may partially deploy IMD 200 to provide a clinician with a visual indication, e.g., via fluoroscopy, of the orientation of IMD 200 prior to deployment of penetrator tine 720A and/or support tines 720C. In some examples, guiding tines 720D may contact selected tissue at the target implant site prior to deployment of penetrating tine 720A. By contacting selected tissue at the target implant site prior to deployment of penetrating tine 720A guiding tines 720D may orient an IMD such that penetrating tine 720A is approximately perpendicular to the selected tissue.

In some examples, a fixation component may include one of more deployment tines. FIGS. 8A and 8B are conceptual diagrams illustrating an example fixation component 802 that includes deployment tines 820D. Fixation component 802 may be the same as or substantially similar to fixation components 202, 302, 502, 602, and/or 702 discussed above in reference to FIGS. 2A-7B, except for the differences describe herein. For example, fixation component 802 includes base 803 from which tines 820 extend. Tines 820 include penetrator tine 820A, protector tine 820B, support tines 820C, and deployment tines 820D. Deployment tines 820D may be spaced apart from penetrator tine 720A an angle within a range from about 20 degrees to about 90 degrees. In some examples, deployment tines 820D may include non-incisive distal ends. Deployment tines are configured to increase a deployment force of IMD 200 to improve, for example, tissue penetration of penetrator tine 820A and/or support tines 820C during deployment. In some examples, tines may include both guiding tines (e.g., guiding tines 720A) and deployment tines 820A. In this way, deployment tins 820A may be added to fixation component 802 to achieve a selected deployment force.

Figure 9:
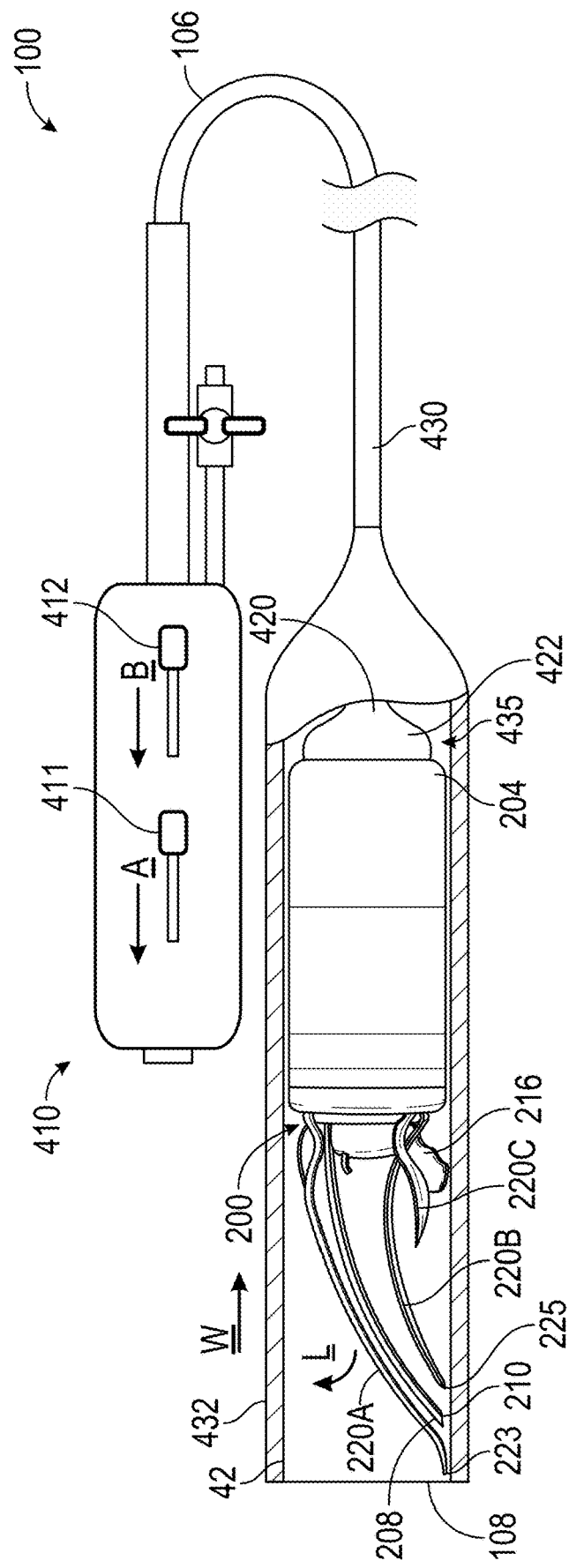
FIG. 9 is a conceptual diagram illustrating a partial cut-away section of an example medical device system including a delivery tool and an IMD.

FIG. 9 is a conceptual diagram illustrating a partial cut-away section of an example medical device system 100 including a delivery tool 106 and an IMD 200. For purposes of illustration, the distal end of delivery tool 106 is enlarged relative to handle 410. Additionally, although medical device system 100 is described in reference to fixation component 202 described in reference to FIGS. 2A-3, in other examples, medical device system 100 may include other fixation components.

During use, IMD 200 is loaded into delivery tool 106 for deployment to a target implant site (e.g. target implant site 102). Delivery tool 106 includes a handle 410, an elongate outer member 430, and an elongate inner member 420 that extends within lumen 435 of outer member 430. Inner member 420 includes a distal end 422, which is configured to engage IMD 200 by abutting proximal end 214 of housing 204 (e.g., as shown in the cut-away section). An entirety of IMD 200 may be loaded within tubular sidewall 432 that defines a distal portion of outer member lumen 430, for example, having been loaded therein by pulling IMD 200, with housing proximal end 214 leading, in through lumen distal opening 108. In some examples, an inner surface 434 of tubular sidewall 432 engages tines 220 of fixation component 202 as IMD 200 is loaded into lumen 435 to deform tines 220 (per arrow L) and then to hold each tine of tines 220 of the loaded IMD 200 in a deformed configuration, e.g., a spring-loaded configuration.

Handle 410 may be configured to control movement of delivery tool 106 and/or deployment of IMD 200. The clinician may position medical device system 100 by advancing delivery tool 106 through vasculature of the patient, for example, from a femoral venous access site and up through the inferior vena cava IVC (FIG. 1), or a radial artery access site. Delivery tool 106 may include articulating features to facilitate the navigation of the distal portion of delivery tool 106. For example, inner member 420 of delivery tool 106 may include a pull wire assembly (not shown) integrated therein and being coupled to another control member 411 of handle 410 that, when moved per arrow A, causes inner member 420 and outer member 430 to bend along distal portions thereof.

In some examples, a proximal end of outer member 430 may be coupled to a control member 412 of handle 410 such that an entirety of outer member 430 is movable with respect to inner member 420, via control member 412. For example, after positioning medical device system 100 at selected tissue in proximity to a target implant site 102 (FIG. 1), a clinician may retract outer member 430, per arrow W, relative to IMD 200 and inner member 420, thereby release the spring loading fixation component 202 to deploy IMD 200 out through distal opening 108 such that tines 220 engage with the selected tissue to secure IMD 200 at the implant site. Additionally, or alternatively, delivery tool 106 may be configured so that a clinician can advance inner member 420 relative to outer member 430 to push IMD 200 out through distal opening 108 for deployment. A length of outer member 430, between handle 410 and distal opening 108 may be between about 100 cm and about 120 cm. Suitable construction detail for a delivery tool like delivery tool 106 is described in U.S. Pat. No. 9,526,522 to Wood et al., which is incorporated herein by reference in its entirety.

Penetrator tine 220A is configured to penetrate or cut a selected tissue to form a puncture. Protector tine 220B is configured to protect first leadlet 208 during deployment. In some examples, during deployment from delivery catheter 106, penetrator tine 220A may initially penetrate selected tissue of atrial surface 103 to form a puncture. Also, protector tine 220B may urge first leadlet 208 toward penetrator tine 220A, thereby guiding leadlet 208 and protector tine 220B into the puncture. For example, protector tine 220B may urge first leadlet 208 toward penetrator tine 220A by applying a force to first leadlet 208 in the direction of penetrator tine 220A during and/or after deployment. By urging first leadlet 208 toward penetrator tine 220A, protector tine 220B may reduce undesired displacement of first leadlet 208 and/or reduce mechanical damage to first leadlet 208 (e.g., as first leadlet 208 passes out of delivery catheter 106). As fixation component 202 is further deployed, penetrator tine 220A and protector tine 220B may return from the deployed configuration, as illustrated in FIG. 3. When in the deployed configuration, first leadlet 208 may extend in a distal direction between penetrator tine 220A and protector tine 220B. In this way, first leadlet 208 extends from distal end 215 of housing 204 of IMD 200 to reach a selected target tissue, such as tissue near ventricular surface 105. Second leadlet 216 may be urged against tissue at atrial surface 103 by penetrator tine 220A and protector tine 220B, and optionally support tine 220C. In this way, IMD 200 may be configured to penetrate the atrioventricular septum to enable pacing and/or sensing at ventricular surface 105 via first electrode 210 and pacing and/or sensing at atrial surface 103 via second electrode 218.

After deployment at target implant site 102, in some examples, a deflection stiffness of tines 220 may enable a clinician to confirm adequate fixation of tines 220 into tissue of a patient. For example, a pull test or tug test may be performed under fluoroscopy to confirm that tines 220 have engaged the tissue to confirm adequacy of implantation of IMD 200. The pull test or tug test may include the clinician pulling or tugging on the deployed IMD 200 and observing movement of tines 220 to determine if tines 220 are engaged in tissue, e.g., tines 220 that are embedded in tissue deflect or bend as deployed IMD 200 is pulled or tugged. By controlling the deflection stiffness, tines 220 may have an improved flexibility that enables a clinician to more easily confirm tissue engagement.

Figure 10:
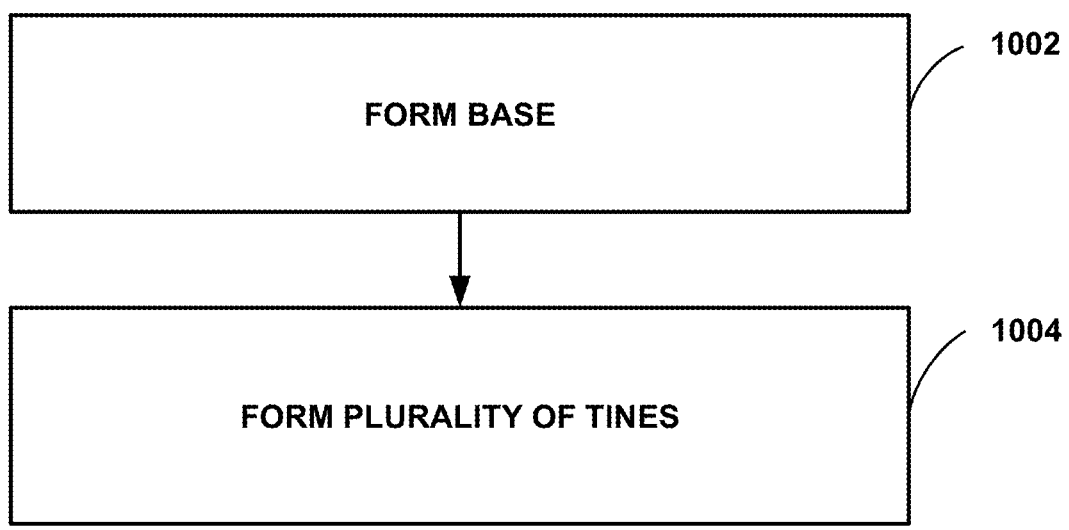
FIG. 10 is a flow diagram illustrating an example method of manufacturing an example fixation component.

The fixation components described herein may be manufactured using any suitable technique. FIG. 10 is a flow diagram illustrating an example method of manufacturing a fixation component 202. Although the technique illustrated in FIG. 10 is described in reference to fixation component 202 illustrated in reference to FIGS. 2A-2F, the technique may be used to manufacture other fixation component, such as fixation component 302, 502, 602, 702, and/or 802 described in reference to FIGS. 4A-8B, and fixation component 202 describe in reference to FIGS. 3A and 3B. Additionally, fixation component 202 and/or fixation component 202 may be manufactured using other techniques.

The technique illustrated in FIG. 10 includes forming base 203 defining longitudinal axis 207 of fixation component 202 (1002). In some examples, forming base 203 may include cutting a tube, such as a metal tube, a nickel titanium alloy tube, or a stainless-steel tube, to define base 203. Forming base 203 may include pre-processing or post-processing steps, such as abrading, coating, heat treating, or polishing a substrate defining base 203.

The technique illustrated in FIG. 10 also includes forming tines 220 extending from base 203 and being spaced apart from one another (1004). In some examples, base 203 and tines 220 may be integrally formed. For example, base 203 and tines 220 may be integrally formed from a tube, such as a metal tube, a nickel titanium alloy tube, or a stainless-steel tube. In some examples, forming base 203 and tines 220 from a single tube may include removing material from the single tube to define base 203 and tines 220. In some examples, removing material from the single tube may include one or more of machining, chemical etching, laser etching, stamping, or water cutting. In some examples, forming tines 220 may include forming one or more tapers on one or more tines of tines 220. For example, forming one or more tapers may include any other above techniques to remove material from the single tube. In some examples, one or more tapers may be formed while removing material form the single tube.

In some examples, forming tines 220 may include bending each tine of tines 220 to define one or more curved section (e.g., first curved section 555A, second curved section 555B, and third curved section 555C, describe above in reference to FIGS. 5A and 5B). In some examples, each curve and/or each tine of tines 520 may be bent individually or bend simultaneously, e.g., by use of a jig configured to bend one or more curves on one or more of tines 220. After bending (and holding in the bent configuration) tines 220, forming tines 220 also may include heat treating the bent tines 220 to cause tines 220 to hold the bent configuration. For example, heat treating the bent tines 220 may cause a microstructure of the material of tines 220 to assume a configuration such that a resting state of tines 220 (e.g., without application of an external force) is the bend configuration.

In some examples, forming tines 220 also may include sharpening distal ends of tines 220. For example, forming penetrator tine 220A may include laser etching distal end 223 to define an infinitely or near infinitely sharp incisive edge (within the tolerances of common manufacturing processes).

In some examples, forming tines 220 also may include forming one or more cutouts, engravings, embossing, or other variations in the thickness of tines 220. For example, cutouts, engravings, embossing, or other variations in the thickness of tines 220 may be formed by laser etching or chemical etching.

Figure 11A:
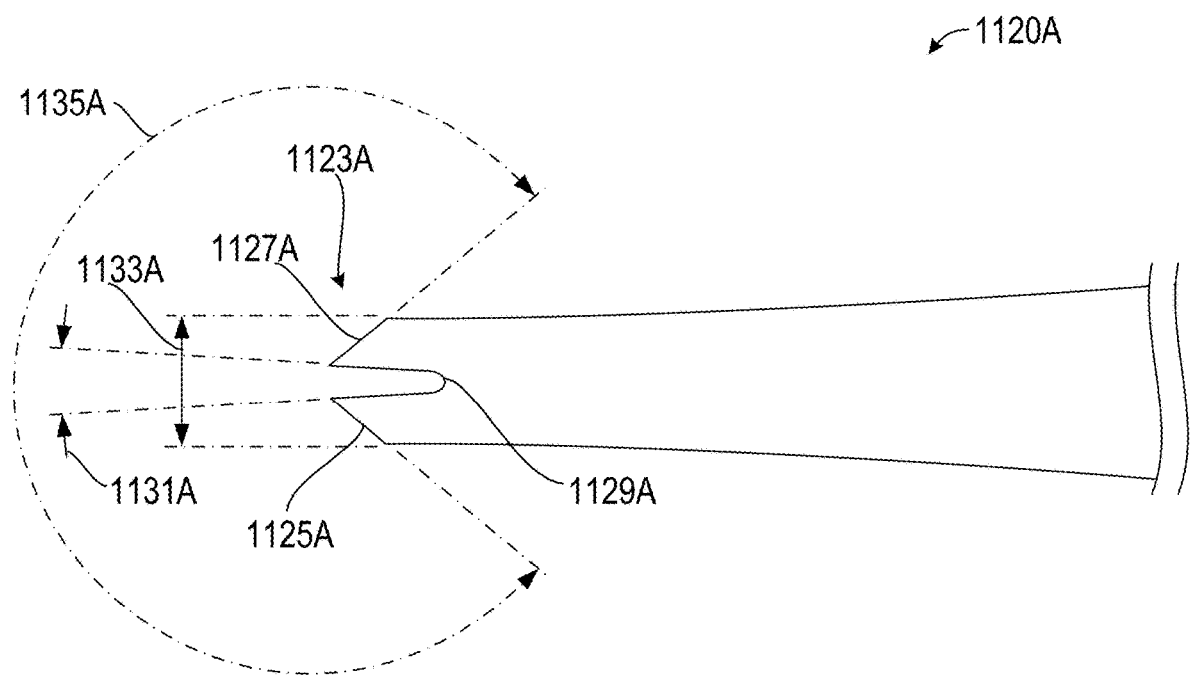
FIGS. 11A and 11B are conceptual diagrams illustrating distal ends of example respective penetrator tines.
Figure 11B:
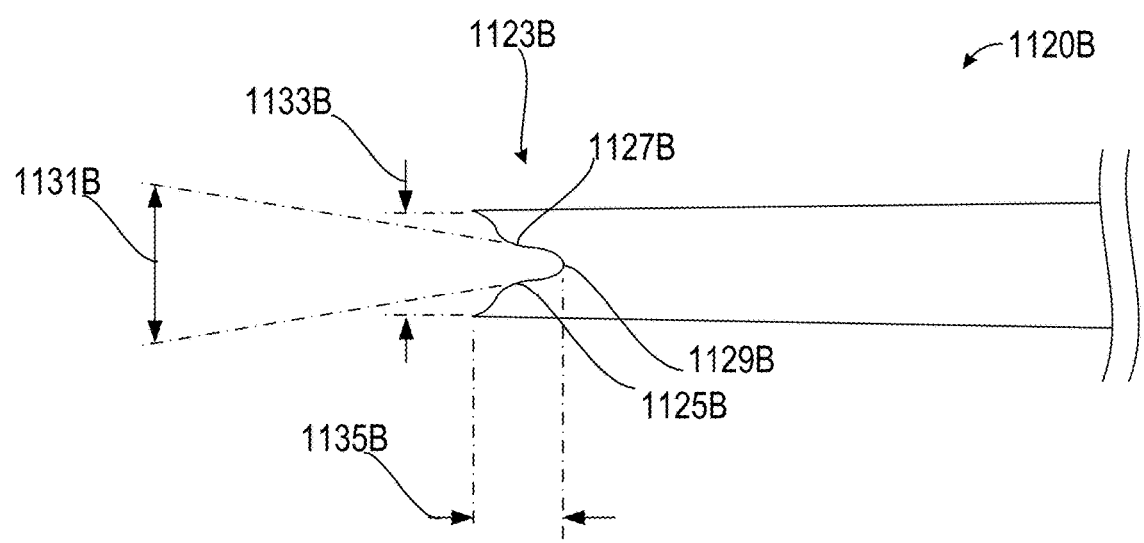

FIGS. 11A and 11B are conceptual diagrams illustrating distal ends 1123A and 1123B of example respective penetrator tines 1120A and 1120B. The distal end of a penetrator tine may include an incisive shape selected to provide a selected tissue penetration in response to a deployment force. Measurements of the selected shape of the curve may include a manufacturing tolerance, such as a common manufacturing tolerance in machining medical device components. As illustrated in FIG. 11A, distal end 1123A of penetrator tine 1120A includes a forked tip. In some examples, a gap 1129A between prongs of the forked tip may have radius within a range from about 0.005 inches (0.127 mm) to about 0.015 inches (0.381 mm), or about 0.01 inches (0.254 mm). The prongs of the forks may be substantially parallel or extend distally at an angle 1131A, such as between about 5 degrees and about 15 degrees, or about 7 degrees. In some examples, a width 1133A of distal end 1123A may be within a range from about 0.04 inches (1.016 mm) and about 0.12 inches (3.048 mm), or about 0.06 inches (1.524 mm). In some examples, leading surfaces 1125A and 1127A (e.g., distal-most surface) may be tapered to a blade, such as, for example a tanto blade shape. In some examples, leading surface 1125A and 1127A may taper from a proximal portion to a distal end at an angle 1135A within a range from about 180 degrees to about 300 degrees, or about 281 degrees.

As illustrated in FIG. 11B, distal end 1123B of penetrator tine 1120B includes a forked tip with curvilinear prongs. In some examples, a gap 1129B between prongs of the forked tip may have radius within a range from about 0.005 inches (0.127 mm) to about 0.015 inches (0.381 mm), or about 0.01 inches (0.254 mm). The prongs of the forks may be substantially parallel or extend distally at an angle 1131B, such as within a range from about 15 degrees to about 25 degrees, or about 19 degrees. In some examples, a length of the prongs of the fork may be within a range from about 0.02 inches (1.016 mm) and about 0.05 inches (3.048 mm), or about 0.038 inches (0.9652 mm). In some examples, a width 1133B of distal end 1123A may be within a range from about 0.04 inches (1.016 mm) and about 0.1 inches (3.048 mm), such as about 0.033 inches (0.8382 mm). In some examples, leading surfaces 1125B and 1127B may be tapered to a blade, such as, for example a curved tanto blade shape.

The following clauses illustrate example subject matter described herein.

Clause 1. A fixation component for an implantable medical device (IMD), comprising: a base defining a longitudinal axis of the fixation component, wherein the base is fixedly attached to the IMD having a proximal end and a distal end aligned along the longitudinal axis; and a plurality of tines extending from the base and being spaced apart from one another, the plurality of tines comprising: a penetrator tine comprising: a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to penetrate a tissue to form a puncture; and a protector tine comprising: a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end, wherein the protector tine is configured to pass the non-incisive distal end through the puncture.

Clause 2. The fixation component of clause 1, wherein the distal section of the protector tine is configured to, when in a deformed configuration, urge a leadlet of the IMD toward the penetrator tine.

Clause 3. The fixation component of clause 1 or 2, wherein a length of the penetrator tine is within a range from about 4 millimeters to about 10 millimeters.

Clause 4. The fixation component of any one of clauses 1 through 3, wherein a width of the penetrator tine tapers from a first width at the proximal section to a second width smaller than the first width at the distal section.

Clause 5. The fixation component of any one of clauses 1 through 4, wherein the distal section of the protector tine is configured to, when in a deformed configuration, urge a leadlet of the IMD toward the penetrator tine, and wherein, when deployed from a deformed configuration to an undeformed configuration, the penetrator tine is configured to pierce the tissue and the protector tine is configured to urge the leadlet into the piercing in the tissue.

Clause 6. The fixation component of any one of clauses 1 through 5, wherein the deformable preset curvature of the penetrator tine comprises a plurality of curves, each respective curve of the plurality of curves defining a respective radius.

Clause 7. The fixation component of clause 6, wherein the curved section of the penetrator tine further comprises at least one straight segment between two curves of the plurality of curves.

Clause 8. The fixation component of clause 6 or 7, wherein at least a first curve of the plurality of curves of the penetrator tine defines a first radius and a second curve of the plurality of curves of the penetrator tine defines a second radius different than the first radius.

Clause 9. The fixation component of any one of clauses 1 through 8, wherein the deformable preset curvature of the protector tine comprises a plurality of curves, each respective curve of the plurality of curves defining a respective radius.

Clause 10. The fixation component of clause 9, wherein the curved section of the protector tine further comprises at least one straight segment between two curves of the plurality of curves.

Clause 11. The fixation component of clause 9 or 10, wherein at least a first curve of the plurality of curves of the penetrator tine defines a first radius and a second curve of the plurality of curves of the penetrator tine defines a second radius different than the first radius.

Clause 12. The fixation component of any one of clauses 1 through 11, wherein the plurality of tines further comprises one or more support tines, wherein the one or more support tines, when in the deployed configuration, are configured to engage the tissue.

Clause 13. The fixation component of clause 12, wherein the one or more support tines are positioned on the base about 45 degrees from the protector tine.

Clause 14. The fixation component of any one of clauses 1 through 13, wherein the plurality of tines further comprises one or more guiding tines configured to at least one of control or indicate an orientation of the fixation component during deployment.

Clause 15. The fixation component of clause 14, wherein the one or more guiding tines are positioned on the base about 180 degrees from the protector tine.

Clause 16. The fixation component of any one of clauses 1 through 15, wherein the plurality of tines further comprises one of more deployment tines configured to increase a deployment force of the fixation component.

Clause 17. The fixation component of clause 16, wherein the deployment tines at positioned on the base about 45 degree from the penetrator tine.

Clause 18. The fixation component of any one of clauses 1 through 17, wherein the distal section of the protector tine is configured to, when in a deformed configuration, urge a leadlet of the IMD toward the penetrator tine, and wherein the protector tine is configured to protect the leadlet when the IMD is loaded into a delivery catheter.

Clause 19. The fixation component of any one of clauses 1 through 18, wherein the tissue comprises a myocardium tissue, and wherein the penetrator tine is configured to penetrate at least one of an interatrial septum, an interventricular septum, or an atrioventricular septum.

Clause 20. The fixation component of any one of clauses 1 through 19, wherein the penetrator tine defines a metal ribbon configured to deform along a plane normal to the longitudinal axis and resist twisting outside of the plane.

Clause 21. The fixation component of any one of clauses 1 through 20, wherein the penetrator tine defines an aperture disposed between the proximal end and the distal end of the penetrator tine.

Clause 22. The fixation component of clause 21, wherein the distal section of the protector tine is configured to, when in a deformed configuration, urge a leadlet of the IMD toward the penetrator tine, wherein the leadlet comprises an elongate member extending from a proximal end mounted in proximity to a distal end of the IMD to a distal end, wherein at least a portion of the leadlet between the proximal end and the distal end thereof extends through the aperture, and wherein the portion of the leadlet is configured to adjust a position of the electrode relative to the penetrator tine or the protector tine.

Clause 23. The fixation component of any one of clauses 1 through 22, wherein the distal section of the penetrator tine extends from the curved section of the penetrator tine at an angle within a range from about 45 degrees to about 135 degrees relative to the longitudinal axis.

Clause 24. An implantable medical device (IMD), comprising: a housing extending along a longitudinal axis from a proximal end to a distal end; an elongate leadlet extending from a proximal end of the leadlet mounted in proximity to the distal end of the housing to a distal end of the leadlet, wherein the distal end of the leadlet comprises a first electrode; a second electrode mounted in proximity to the distal end of the housing; a fixation component comprising: a base defining a longitudinal axis of the fixation component, wherein the base is fixedly attached to the IMD having a proximal end and a distal end aligned along the longitudinal axis; and a plurality of tines extending from the base and being spaced apart from one another, the plurality of tines comprising: a penetrator tine comprising: a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to penetrate a tissue to form a puncture; and a protector tine comprising: a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end, wherein the protector tine is configured to pass the non-incisive distal end through the puncture.

Clause 25. The IMD of clause 24, wherein the distal section of the protector tine is configured to, when in a deformed configuration, urge a leadlet of the IMD toward the penetrator tine.

Clause 26. The IMD of clause 24 or 25, wherein the leadlet comprises a first leadlet, wherein the IMD further comprises a second leadlet extending from a proximal end of the second leadlet mounted in proximity to the distal end of the housing to a distal end of the second leadlet comprising the second electrode, the second leadlet comprising a deflection member having a deformable preset curvature.

Clause 27. The IMD of clauses 26, wherein, when in the undeformed configuration, the deflection member urges the second electrode to extend laterally outward from the longitudinal axis.

Clause 28. The IMD of clause 26 or 27, wherein the elongate body of the second electrode defines a notch configured to, when the deflection member urges the second electrode for a deformed configuration to extend laterally outward from the longitudinal axis to the undeformed configuration, reduce shear stress in at least a portion of the elongate body of the second electrode.

Clause 29. The IMD of any one of clauses 24 through 28, wherein the protector tine defines an aperture size to allow the second electrode to extend through the aperture when the protector tine and the second electrode are in the undeformed configuration.

Clause 30. The IMD of any one of clauses 24 through 29, wherein the first electrode is configured to at least one of deliver stimulation therapy to or sense cardiac signals of a ventricle of a heart when the IMD is implanted within an atrium of the heart.

Clause 31. The IMD of any one of clauses 24 through 30, wherein the second electrode is configured to at least one of deliver stimulation therapy to or sense cardiac signals of an atrium of a heart when the IMD is implanted within an atrium of the heart.

Clause 32. The IMD of any one of clauses 24 through 31, wherein the fixation component comprises the fixation component of any one of clauses 2 through 23.

Clause 33. A medical device system comprising: an implantable medical device (IMD) comprising: a housing extending along a longitudinal axis from a proximal end to a distal end; an elongate leadlet extending from a proximal end of the leadlet mounted in proximity to the distal end of the housing to a distal end of the leadlet, wherein the distal end of the leadlet comprises a first electrode; a second electrode mounted in proximity to the distal end of the housing; and a fixation component comprising a base in proximity to the distal end of the housing and a plurality of tines fixedly attached spaced from one another around a perimeter of the distal end of the housing; and a delivery tool comprising a tubular sidewall that defines a lumen into which the IMD may be loaded, wherein the lumen having a distal opening through which the IMD may be deployed, wherein the plurality of tines comprises: a penetrator tine comprising: a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to penetrate a tissue to form a puncture; and a protector tine comprising: a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end, wherein the protector tine is configured to pass the non-incisive distal end through the puncture.

Clause 34. The medical device system of clause 33, wherein the IMD comprises the IMD of any one of clauses 24 through 32.

Clause 35. A method of forming a fixation component for an IMD comprising: forming a base defining a longitudinal axis of the fixation component; and forming a plurality of tines extending from the base and being spaced apart from one another, the plurality of tines comprising: a penetrator tine comprising: a proximal section of the penetrator tine fixedly attached to the base and extending from the base in a first direction; a curved section of the penetrator tine defining a deformable preset curvature of the penetrator tine and extending laterally from the proximal section of the penetrator tine and traversing the longitudinal axis; and a distal section of the penetrator tine extending from the curved section of the penetrator tine and terminating in an incisive distal end, wherein the incisive distal end is configured to penetrate a tissue to form a puncture; and a protector tine comprising: a proximal section of the protector tine fixedly attached to the base and extending from the base in the first direction; a curved section of the protector tine defining a deformable preset curvature of the protector tine and extending from the proximal section of the protector tine laterally, outward from the longitudinal axis; and a distal section of the protector tine extending from the curved section of the protector tine and terminating in a non-incisive distal end, wherein the protector tine is configured to pass the non-incisive distal end through the puncture.

Clause 36. The method of clause 35, wherein forming the plurality of tines further comprises sharpening the distal end of the penetrator tine.

Clause 37. The method of clause 35 or 36, wherein forming the plurality of tines further comprises forming in the penetrator tine or the protector tine at least one of a cutout, an engraving, an embossing, or variation in thickness of the respective tine.

Clause 38. The method of any one of clauses 35 through 37, wherein the fixation component comprises the fixation component of any one of clauses 2 through 23.

Various examples of the disclosure have been described. Any combination of the described systems, operations, or functions is contemplated. These and other examples are within the scope of the following claims.

What is claimed is:

1. A fixation component for an implantable medical device (IMD), comprising:
   a base defining a longitudinal axis of the fixation component, wherein the base is configured to be fixedly attached to the IMD; and
   a plurality of tines extending from the base and being spaced apart from one another, the plurality of tines comprising:
      a penetrator tine comprising:
         a proximal section of the penetrator tine fixedly attached to the base and extending from the base in a first direction;
         a curved section of the penetrator tine defining a deformable preset curvature of the penetrator tine and extending laterally from the proximal section of the penetrator tine and traversing the longitudinal axis; and
         a distal section of the penetrator tine extending from the curved section of the penetrator tine and terminating in an incisive distal end, wherein the incisive distal end is configured to penetrate a tissue to form a puncture; and
      a protector tine comprising:
         a proximal section of the protector tine fixedly attached to the base and extending from the base in the first direction;
         a curved section of the protector tine extending from the proximal section of the protector tine laterally, outward from the longitudinal axis; and
         a distal section of the protector tine extending from the curved section of the protector tine and terminating in a non-incisive distal end,
         wherein the distal section of the protector tine is configured to, when in a deformed configuration, urge a leadlet of the IMD toward the penetrator tine.

2. The fixation component of claim 1, wherein a length of the penetrator tine is within a range from 4 millimeters to 10 millimeters.

3. The fixation component of claim 1, wherein a width of the penetrator tine tapers from a first width at the proximal section to a second width smaller than the first width at the distal section.

4. The fixation component of claim 1, wherein, when deployed from a deformed configuration to an undeformed configuration, the penetrator tine is configured to pierce the tissue and the protector tine is configured to urge the leadlet into the piercing in the tissue.

5. The fixation component of claim 1, wherein the deformable preset curvature of the penetrator tine comprises a plurality of curves, each respective curve of the plurality of curves defining a respective radius.

6. The fixation component of claim 5, wherein the curved section of the penetrator tine further comprises at least one straight segment between two curves of the plurality of curves.

7. The fixation component of claim 5, wherein at least a first curve of the plurality of curves of the penetrator tine defines a first radius and a second curve of the plurality of curves of the penetrator tine defines a second radius different than the first radius.

8. The fixation component of claim 1, wherein the curved section of the protector tine defines a deformable preset curvature of the protector tine, and wherein the deformable preset curvature of the protector tine comprises a plurality of curves, each respective curve of the plurality of curves defining a respective radius.

9. The fixation component of claim 8, wherein the curved section of the protector tine further comprises at least one straight segment between two curves of the plurality of curves.

10. The fixation component of claim 8, wherein at least a first curve of the plurality of curves of the penetrator tine defines a first radius and a second curve of the plurality of curves of the penetrator tine defines a second radius different than the first radius.

11. The fixation component of claim 1, wherein the plurality of tines further comprises one or more support tines, wherein the one or more support tines, when in the deployed configuration, are configured to engage the tissue.

12. The fixation component of claim 11, wherein the one or more support tines are positioned on the base 45 degrees from the protector tine.

13. The fixation component of claim 1, wherein the plurality of tines further comprises one or more guiding tines configured to at least one of control or indicate an orientation of the fixation component during deployment.

14. The fixation component of claim 13, wherein the one or more guiding tines are positioned on the base 180 degrees from the protector tine.

15. The fixation component of claim 1, wherein the plurality of tines further comprises one of more deployment tines configured to increase a deployment force of the fixation component.

16. The fixation component of claim 15, wherein the deployment tines are positioned on the base 45 degree from the penetrator tine.

17. The fixation component of claim 1, wherein the protector tine is configured to protect the leadlet when the IMD is loaded into a delivery catheter.

18. The fixation component of claim 1, wherein the tissue comprises a myocardium tissue, and wherein the penetrator tine is configured to penetrate at least one of an interatrial septum, an interventricular septum, or an atrioventricular septum.

19. The fixation component of claim 1, wherein the penetrator tine defines a metal ribbon configured to deform along a plane normal to the longitudinal axis and resist twisting outside of the plane.

20. The fixation component of claim 1, wherein the penetrator tine defines an aperture disposed between the proximal end and the distal end of the penetrator tine.

21. The fixation component of claim 20, wherein the leadlet comprises an elongate member extending from a proximal end of the fixation component and configured to be mounted in proximity to a distal end of the IMD to a distal end, wherein at least a portion of the leadlet between the proximal end and the distal end thereof extends through the aperture, and wherein the portion of the leadlet is configured to adjust a position of the electrode relative to the penetrator tine or the protector tine.

22. The fixation component of claim 1, wherein the distal section of the penetrator tine extends from the curved section of the penetrator tine at an angle within a range from 45 degrees to 135 degrees relative to the longitudinal axis.

23. An implantable medical device (IMD), comprising:
a housing extending along a longitudinal axis from a proximal end to a distal end;
an elongate leadlet mounted in proximity to the distal end of the housing and extending distally from the housing, wherein a distal end of the leadlet comprises a first electrode;
a second electrode mounted in proximity to the distal end of the housing;
a fixation component comprising:
a base defining a longitudinal axis of the fixation component, wherein the base is fixedly attached to the IMD having a proximal end and a distal end aligned along the longitudinal axis; and
a plurality of tines extending from the base and being spaced apart from one another, the plurality of tines comprising:
a penetrator tine comprising:
a proximal section of the penetrator tine fixedly attached to the base and extending from the base in a first direction;
a curved section of the penetrator tine defining a deformable preset curvature of the penetrator tine and extending laterally from the proximal section of the penetrator tine and traversing the longitudinal axis; and
a distal section of the penetrator tine extending from the curved section of the penetrator tine and terminating in an incisive distal end,
wherein the incisive distal end is configured to penetrate a tissue to form a puncture; and
a protector tine comprising:
a proximal section of the protector tine fixedly attached to the base and extending from the base in the first direction;
a curved section of the protector tine extending from the proximal section of the protector tine laterally, outward from the longitudinal axis; and
a distal section of the protector tine extending from the curved section of the protector tine and terminating in a non-incisive distal end,
wherein the distal section of the protector tine is configured to,
when in a deformed configuration, urge the leadlet toward the penetrator tine.

24. The IMD of claim 23, wherein the leadlet comprises a first leadlet, wherein the IMD further comprises a second leadlet mounted to and extending distally from the distal end of the housing and terminating in a distal end comprising the second electrode, the second leadlet comprising a deflection member having a deformable preset curvature.

25. The IMD of claim 24, wherein, when in the undeformed configuration, the deflection member urges the second electrode to extend laterally outward from the longitudinal axis.

26. The IMD of claim 23, wherein the protector tine defines an aperture size to allow the second electrode to extend through the aperture when the protector tine and the second electrode are in the undeformed configuration.

27. The IMD of claim 23, wherein the first electrode is configured to at least one of deliver stimulation therapy to or sense cardiac signals of a ventricle or an atrium of a heart when the IMD is implanted within an atrium of the heart.

28. A medical device system comprising:
an implantable medical device (IMD) comprising:
a housing extending along a longitudinal axis from a proximal end to a distal end;
an elongate leadlet mounted in proximity to the distal end of the housing and extending distally from the housing, wherein a distal end of the leadlet comprises a first electrode;
a second electrode mounted in proximity to the distal end of the housing; and
a fixation component comprising a base in proximity to the distal end of the housing and a plurality of tines fixedly attached spaced from one another around a perimeter of the distal end of the housing; and
a delivery tool comprising a tubular sidewall that defines a lumen into which the IMD may be loaded, wherein the lumen having a distal opening through which the IMD may be deployed,
wherein the plurality of tines comprises:
a penetrator tine comprising:
a proximal section of the penetrator tine fixedly attached to the base and extending from the base in a first direction;
a curved section of the penetrator tine defining a deformable preset curvature of the penetrator tine and extending laterally from the proximal section of the penetrator tine and traversing the longitudinal axis; and
a distal section of the penetrator tine extending from the curved section of the penetrator tine and terminating in an incisive distal end, wherein the incisive distal end is configured to penetrate a tissue to form a puncture; and
a protector tine comprising:
a proximal section of the protector tine fixedly attached to the base and extending from the base in the first direction;
a curved section of the protector tine extending from the proximal section of the protector tine laterally, outward from the longitudinal axis; and
a distal section of the protector tine extending from the curved section of the protector tine and terminating in a non-incisive distal end,
wherein the distal section of the protector tine is configured to, when in a deformed configuration, urge the leadlet toward the penetrator tine.

29. A method of forming a fixation component for an IMD comprising:
  forming a base defining a longitudinal axis of the fixation component; and
  forming a plurality of tines extending from the base and being spaced apart from one another, the plurality of tines comprising:
    a penetrator tine comprising:
      a proximal section of the penetrator tine fixedly attached to the base and extending from the base in a first direction;
      a curved section of the penetrator tine defining a deformable preset curvature of the penetrator tine and extending laterally from the proximal section of the penetrator tine and traversing the longitudinal axis; and
      a distal section of the penetrator tine extending from the curved section of the penetrator tine and terminating in an incisive distal end, wherein the incisive distal end is configured to penetrate a tissue to form a puncture; and
    a protector tine comprising:
      a proximal section of the protector tine fixedly attached to the base and extending from the base in the first direction;
      a curved section of the protector tine extending from the proximal section of the protector tine laterally, outward from the longitudinal axis; and
      a distal section of the protector tine extending from the curved section of the protector tine and terminating in a non-incisive distal end,
      wherein the distal section of the protector tine is configured to, when in a deformed configuration, urge a leadlet of the IMD toward the penetrator tine.

30. The method of claim 29, wherein forming the plurality of tines further comprises sharpening the distal end of the penetrator tine.

31. The method of claim 29, wherein forming the plurality of tines further comprises forming in the penetrator tine or the protector tine at least one of a cutout, an engraving, an embossing, or variation in thickness of the respective tine.

32. The fixation component of claim 1, wherein the curved section of the protector tine defines a deformable preset curvature of the protector tine, and wherein the protector tine is configured to pass the non-incisive distal end through the puncture.

33. The IMD of claim 23, wherein the curved section of the protector tine defines a deformable preset curvature of the protector tine, and wherein the protector tine is configured to pass the non-incisive distal end through the puncture.

\* \* \* \* \*